`US009481729B2`

(12) United States Patent
Zhang

(10) Patent No.: US 9,481,729 B2
(45) Date of Patent: Nov. 1, 2016

(54) ANTI-HER2 AND ANTI-IGF-IR BI-SPECIFIC ANTIBODIES AND USES THEREOF

(71) Applicant: The University of Hong Kong, Hong Kong (CN)

(72) Inventor: Mei-Yun Zhang, Hong Kong (CN)

(73) Assignee: The University of Hong Kong, Hong Kong (HK)

( * ) Notice: Subject to any disclaimer, the term of this patent is extended or adjusted under 35 U.S.C. 154(b) by 0 days.

(21) Appl. No.: 14/483,330

(22) Filed: Sep. 11, 2014

(65) Prior Publication Data

US 2015/0071927 A1 Mar. 12, 2015

Related U.S. Application Data

(60) Provisional application No. 61/876,564, filed on Sep. 11, 2013.

(51) Int. Cl.
*A61K 39/395* (2006.01)
*C07K 16/28* (2006.01)
*C07K 16/32* (2006.01)

(52) U.S. Cl.
CPC .......... *C07K 16/2863* (2013.01); *C07K 16/32* (2013.01); *C07K 2317/31* (2013.01); *C07K 2317/526* (2013.01); *C07K 2317/73* (2013.01); *C07K 2317/732* (2013.01); *C07K 2317/76* (2013.01); *G01N 2333/475* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,530,101 A | 6/1996 | Queen | |
| 5,565,332 A | 10/1996 | Hoogenboom | |
| 5,585,089 A | 12/1996 | Queen | |
| 5,766,886 A | 6/1998 | Studnicka | |
| 5,804,440 A | 9/1998 | Burton | |
| 6,407,213 B1 | 6/2002 | Carter | |
| 2005/0037000 A1 | 2/2005 | Stavenhagen | |
| 2005/0064514 A1 | 3/2005 | Stavenhagen | |
| 2010/0331527 A1* | 12/2010 | Davis | C07K 16/2809 530/387.3 |
| 2011/0135663 A1* | 6/2011 | Zhang | C07K 16/2863 424/172.1 |
| 2012/0251541 A1* | 10/2012 | Baurin | C07K 16/00 424/136.1 |

FOREIGN PATENT DOCUMENTS

| | | |
|---|---|---|
| EP | 239400 | 9/1987 |
| EP | 519596 | 12/1992 |
| EP | 592106 | 4/1994 |
| WO | 9109967 | 7/1991 |
| WO | 9317105 | 9/1992 |
| WO | 2013/033008 * | 3/2013 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Bender and Nahta, "Her2 cross talk and therapeutic resistance in breast cancer", Front. Biosci., 13:3906-12 (2008).
Casa, et al., "The type I insulin-like growth factor receptor pathway: a key player in cancer therapeutic resistance", Front. Biosci., 13:3273-87 (2008).
Chothia and Lesk, "Canonical structures for the hypervariable regions of immunoglobulins", J. Mol. Biol., 196:901-17 (1987).
Clynes, et al., "Inhibitory Fc receptors modulate in vivo cytotoxicity against tumor targets", Nat Med., 6:443-6 (2000).
Hollinger and Hudson, "Engineered antibody fragments and the rise of single domains", Nature Biotech., 23(9):1126-36 (2005).
Huang. et al., "Heterotrimerization of the growth factor receptors erbB2, erbB3, and insulin-like growth factor-i receptor in breast cancer cells resistant to herceptin", Cancer Res., 70:1204-14 (2010).
Hudis, "Trastuzumab—mechanism of action and use in clinical practice", N. Engl. J. Med., 357:39-51 (2007).
Jin and Esteva, "Cross-talk between the ErbB/HER family and the type I insulin-like growth factor receptor signaling pathway in breast cancer", J. Mammary Gland. Biol, Neoplasia., 13:485-98 (2008).
Kute, et al., "Development of Herceptin resistance in breast cancer cells", Cytometry A., 57:86-93 (2004).
Ridgeway, et al., "'Knobs-into-holes' engineering of antibody CH3 domains for heavy chain heterodimerization", Protein Eng., 9:671-21, (1996).
Riechmann, et al., "Reshaping Human Antibodies for Therapy," Nature, 332:323-7 (1988).
Stern, "Improving treatment of HER2-positive cancers: opportunities and challenges", Sci. Transl. ed., 4:127rv2 (2012).
Tan, et al., "Superhumanized" antibodies: reduction of immunogenic potential by complementarity-determining region grafting with human germline sequences: application to an anti-CD28, J. Immunol. 169:1119-25 (2002).
Tokunaga, et al., "Trastuzumab and breast cancer: developments and current status", Int. J. Clin. Oncol., 11:199-208 (2006).
Zack, et al., "Novel structural features of autoantibodies in murine lupus: a possible superantigen binding site", Immunol Cell Biol.,, 72:513-20 (1994).
Zhang, et al., "Characterization of a chimeric monoclonal antibody against the insulin-like growth factor-I receptor", MAbs., 1:475-80 (2009).

\* cited by examiner

*Primary Examiner* — Sheela J Huff
(74) *Attorney, Agent, or Firm* — Pabst Patent Group LLP

(57) ABSTRACT

Disclosed are antibodies, or binding fragments thereof, that specifically bind to human HER2 and human IGF-IR. Also provided are nucleic acid molecules encoding the disclosed antibodies and binding fragments and vectors and host cells containing these nucleic acid molecules. The disclosure also provides methods of inhibiting cancer cell growth and metastasis in a mammal using the antibodies described herein, as well as compositions containing the antibodies, nucleic acid molecules encoding the antibodies, and host cells and vectors comprising the nucleic acid molecules. The disclosure also features the use of the polypeptides to detect the presence of HER2 and IGF-IR in a mammal, and epitopes that can be used as cancer vaccine immunogens.

13 Claims, 4 Drawing Sheets

SEQUENCE LISTING

<160> NUMBER OF SEQ ID NOS: 20

<210> SEQ ID NO 1
<211> LENGTH: 449
<212> TYPE: PRT
<213> ORGANISM: Artificial Sequence
<220> FEATURE:
<223> OTHER INFORMATION: HC1 region of the Herceptin antibody

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Lys

<210> SEQ ID NO 2
<211> LENGTH: 214
<212> TYPE: PRT
<213> ORGANISM: Artificial Sequence
<220> FEATURE:
<223> OTHER INFORMATION: LC1 region of the Herceptin antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
```

```
                100                 105                 110
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 3
<211> LENGTH: 455
<212> TYPE: PRT
<213> ORGANISM: Artificial Sequence
<220> FEATURE:
<223> OTHER INFORMATION: HC region of m590 antibody

<400> SEQUENCE: 3

Glu Val Gln Leu Gln Gln Ser Gly Pro Glu Leu Gln Pro Gly Ser
1               5                   10                  15

Ser Val Lys Ile Ser Cys Lys Ala Ser Gly Tyr Ser Phe Thr Ala Tyr
                20                  25                  30

Tyr Met His Trp Val Lys Gln Ser His Gly Lys Ser Leu Glu Trp Ile
            35                  40                  45

Gly Arg Ile Asn Pro Asp Asn Gly Asn Ser Tyr Asn Gln Lys Phe
        50                  55                  60

Lys Gly Lys Ala Ile Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ala Lys Ser Thr Ser Tyr Asp Tyr Asp Gly Tyr Trp Tyr Phe Asp Val
            100                 105                 110

Trp Gly Ala Gly Thr Thr Val Thr Val Ser Ser Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
```

```
                245                 250                 255
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 4
<211> LENGTH: 213
<212> TYPE: PRT
<213> ORGANISM: Artificial Sequence
<220> FEATURE:
<223> OTHER INFORMATION: LC region of m590 antibody

<400> SEQUENCE: 4

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Ile
            20                  25                  30

His Trp Phe Gln Gln Lys Pro Gly Thr Ser Pro Lys Val Trp Ile Tyr
        35                  40                  45

Gly Thr Ser Asn Leu Ala Ser Gly Val Pro Ala Arg Phe Thr Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
```

```
              145                 150                 155                 160
        Ser Val Thr Glu Gln Asp Ser Lys Asp Ser Thr Tyr Ser Leu Ser Ser
                            165                 170                 175

Thr Leu Thr Leu Ser Lys Ala Asp Tyr Glu Lys His Lys Val Tyr Ala
                        180                 185                 190

Cys Glu Val Thr His Gln Gly Leu Ser Leu Pro Val Thr Lys Ser Leu
                    195                 200                 205

Asn Arg Arg Glu Cys
                210

<210> SEQ ID NO 5
<211> LENGTH: 107
<212> TYPE: PRT
<213> ORGANISM: Homo sapiens

<400> SEQUENCE: 5

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: CH3 constant region of an anti-human-HER2
      antibody

<400> SEQUENCE: 6

Gly Gln Pro Arg Glu Pro Gln Val Tyr Thr Leu Pro Pro Ser Arg Asp
1               5                   10                  15

Glu Leu Thr Lys Asn Gln Val Ser Leu Tyr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 107
<212> TYPE: PRT
```

```
<213> ORGANISM: Artificial Sequence
<220> FEATURE:
<223> OTHER INFORMATION: CH3 constant region of an anti-human-IGF-IR
      antibody

<400> SEQUENCE: 7

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Thr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 8
<211> LENGTH: 1957
<212> TYPE: DNA
<213> ORGANISM: Artificial Sequence
<220> FEATURE:
<223> OTHER INFORMATION: HC1 region of the Herceptin antibody

<400> SEQUENCE: 8
gaagtgcagc tggtcgaatc cggaggagga ctggtgcagc caggagggtc cctgcggctg      60
tcttgcgccg ctagtggctt aacatcaaa  gacacctaca ttcactgggt cgcccaggca     120
ccagggaagg gactggagtg ggtcgctcga atctatccta caaatggata cactcgatat     180
gccgacagcg tgaaaggccg gtttactatt tcagcagata ccagcaagaa cacagcctac     240
ctgcagatga acagcctgag agccgaagat acagctgtgt actattgttc aggtggggga     300
ggcgacggct tctacgcaat ggattattgg ggccagggga ctctggtgac cgtgagctca     360
gcttccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttggtgag     660
aggccagcac aggagggagg ggtgtctgct ggaagccagg ctcagcgctc ctgcctggac     720
gcatcccggc tatgcagccc cagtccaggg cagcaaggca ggccccgtct gcctcttcac     780
ccggagcctc tgcccgcccc actcatgctc agggagaggg tcttctggct ttttccccag     840
gctctgggca ggcacaggct aggtgcccct aacccaggcc ctgcacacaa aggggcaggt     900
gctgggctca gacctgccaa gagccatatc cgggaggacc ctgcccctga cctaagccca     960
ccccaaaggc caaactctcc actccctcag ctcggacacc ttctctcctc ccagattcga    1020
gtaactccca atcttctctc tgcagagccc aaatcttgtg acaaaactca cacatgccca    1080
ccgtgcccag gtaagccagc ccaggcctcg ccctccagct caaggcggga caggtgccct    1140
agagtagcct gcatccaggg acaggcccca gccgggtgct gacacgtcca cctccatctc    1200
ttcctcagca cctgaactcc tggggggacc gtcagtcttc ctcttccccc caaaacccaa    1260
```

```
ggacaccctc atgatctccc ggacccctga ggtcacatgc gtggtggtgg acgtgagcca    1320
cgaagaccct gaggtcaagt tcaactggta cgtggacggc gtggaggtgc ataatgccaa    1380
gacaaagccg cgggaggagc agtacaacag cacgtaccgg gtggtcagcg tcctcaccgt    1440
cctgcaccag gactggctga atggcaagga gtacaagtgc aaggtctcca acaaagccct    1500
cccagccccc atcgagaaaa ccatctccaa agccaaggt gggacccgtg gggtgcgagg     1560
gccacatgga cagaggccgg ctcggcccac cctctgccct gagagtgacc gctgtaccaa    1620
cctctgtcct acagggcagc ccgagaacc acaggtgtac accctgcccc catcccggga    1680
tgagctgacc aagaaccagg tcagcctgac ctgcctggtc aaaggcttct atcccagcga    1740
catcgccgtg gagtgggaga gcaatgggca gccggagaac aactacaaga ccacgcctcc    1800
cgtgctggac tccgacggct ccttcttcct ctacagcaag ctcaccgtgg acaagagcag    1860
gtggcagcag gggaacgtct tctcatgctc cgtgatgcat gaggctctgc acaaccacta    1920
cacgcagaag agcctctccc tgtctccggg taaatga                             1957
```

<210> SEQ ID NO 9
<211> LENGTH: 645
<212> TYPE: DNA
<213> ORGANISM: Artificial Sequence
<220> FEATURE:
<223> OTHER INFORMATION: LC1 region of the Herceptin antibody

<400> SEQUENCE: 9

```
gatatccaga tgacccagag cccatctagt ctgagtgcct cagtgggcga cagggtcact     60
attacctgtc gcgcttccca ggatgtgaac accgctgtcg catggtacca gcagaagcct    120
gggaaagctc caaagctgct gatctacagc gcatccttcc tgtattccgg agtgccatct    180
cggttttctg ggagtagatc aggaacagac ttcacactga ctatttcaag cctgcagccc    240
gaggattttg ccacttacta ttgccagcag cactatacca ccccctac attcggacag      300 ggcactaaag tggagatcaa gaggaccgtg gcagccccct ctgtcttcat ttttccaccc    360
agtgacgaac agctgaagag tggcacagcc tcagtggtct gtctgctgaa caatttctac    420
cctcgcgaag caaaagtgca gtggaaggtc gataacgccc tgcagagcgg caacagccag    480
gagtctgtga ccgaacagga cagtaaagat tcaacatata gcctgtcctc taccctgaca    540
ctgtccaagg ctgactacga aagcataaa gtgtatgcat gcgaagtcac ccatcagggg     600
ctgtcatcac cagtcaccaa atctttaat aggggagagt gctaa                     645
```

<210> SEQ ID NO 10
<211> LENGTH: 1975
<212> TYPE: DNA
<213> ORGANISM: Artificial Sequence
<220> FEATURE:
<223> OTHER INFORMATION: HC region of m590 antibody

<400> SEQUENCE: 10

```
gaggtccagc tgcaacagtc tggacctgag ctggagcagc ctgggtcttc agtgaagata     60
tcctgcaagg cttctggtta ctcattcact gcctactaca tgcactgggt gaaacagagc    120
catgaaaaga gccttgagtg gattggacgt attaatcctg acaatggtgg taacagctac    180
aaccagaagt tcaagggcaa ggccatatta actgtagaca agtcatccaa cacagcctac    240
atggaactcc gcagcctgac atctgaggac tctgcggtct attactgtgc aaagtcaacc    300
tcctatgatt acgacggtta ctggtacttc gatgtctggg gcgcagggac cacggtcacc    360
```

| | |
|---|---|
| gtctcctcag tgagctcagc ttccaccaag ggcccatcgg tcttccccct ggcaccctcc | 420 |
| tccaagagca cctctggggg cacagcggcc ctgggctgcc tggtcaagga ctacttcccc | 480 |
| gaaccggtga cggtgtcgtg aactcaggc gccctgacca gcggcgtgca caccttcccg | 540 |
| gctgtcctac agtcctcagg actctactcc ctcagcagcg tggtgaccgt gccctccagc | 600 |
| agcttgggca cccagaccta catctgcaac gtgaatcaca agcccagcaa caccaaggtg | 660 |
| gacaagaaag ttggtgagag gccagcacag ggagggaggg tgtctgctgg aagccaggct | 720 |
| cagcgctcct gcctggacgc atcccggcta tgcagcccca gtccagggca gcaaggcagg | 780 |
| ccccgtctgc ctcttcaccc ggagcctctg cccgccccac tcatgctcag ggagagggtc | 840 |
| ttctggcttt ttccccaggc tctgggcagg cacaggctag gtgcccctaa cccaggccct | 900 |
| gcacacaaag gggcaggtgc tgggctcaga cctgccaaga gccatatccg ggaggaccct | 960 |
| gcccctgacc taagcccacc ccaaaggcca aactctccac tccctcagct cggacacctt | 1020 |
| ctctcctccc agattcgagt aactcccaat cttctctctg cagagcccaa atcttgtgac | 1080 |
| aaaactcaca catgcccacc gtgcccaggt aagccagccc aggcctcgcc ctccagctca | 1140 |
| aggcgggaca ggtgccctag agtagcctgc atccagggac aggccccagc cgggtgctga | 1200 |
| cacgtccacc tccatctctt cctcagcacc tgaactcctg gggggaccgt cagtcttcct | 1260 |
| cttccccca aaacccaagg acaccctcat gatctcccgg acccctgagg tcacatgcgt | 1320 |
| ggtggtggac gtgagccacg aagaccctga ggtcaagttc aactggtacg tggacggcgt | 1380 |
| ggaggtgcat aatgccaaga caaagccgcg ggaggagcag tacaacagca cgtaccgggt | 1440 |
| ggtcagcgtc ctcaccgtcc tgcaccagga ctggctgaat ggcaaggagt acaagtgcaa | 1500 |
| ggtctccaac aaagccctcc cagcccccat cgagaaaacc atctccaaag ccaaaggtgg | 1560 |
| gacccgtggg gtgcgagggc cacatggaca gaggccggct cggcccaccc tctgccctga | 1620 |
| gagtgaccgc tgtaccaacc tctgtcctac agggcagccc cgagaaccac aggtgtacac | 1680 |
| cctgccccca tcccgggatg agctgaccaa gaaccaggtc agcctgacct gcctggtcaa | 1740 |
| aggcttctat cccagcgaca tcgccgtgga gtgggagagc aatgggcagc cggagaacaa | 1800 |
| ctacaagacc acgcctcccg tgctggactc cgacggctcc ttcttcctct acagcaagct | 1860 |
| caccgtggac aagagcaggt ggcagcaggg gaacgtcttc tcatgctccg tgatgcatga | 1920 |
| ggctctgcac aaccactaca cgcagaagag cctctccctg tctccgggta aatga | 1975 |

<210> SEQ ID NO 11
<211> LENGTH: 639
<212> TYPE: DNA
<213> ORGANISM: Artificial Sequence
<220> FEATURE:
<223> OTHER INFORMATION: LC region of m590 antibody

<400> SEQUENCE: 11

| | |
|---|---|
| caaattgttc tcacccagtc tccagcaatc atgtctgcat ctccagggga gaaggtcacc | 60 |
| ataacctgca gtgccagctc aagtgtaagt tacatacact ggttccagca gaagccaggc | 120 |
| acttctccca agtctggatt tatggcacg tccaacctgg cttctggagt ccctgctcgc | 180 |
| ttcactggca gtggatctgg gacctcttac tctctcacaa tcagccgaat ggaggctgaa | 240 |
| gatgctgcca cttattactg ccaacaaagg agtagttacc cattcacgtt cggctcgggg | 300 |
| acaaagttgg aaataaaacg gactgtggct gcaccatctg tcttcatctt cccgccatct | 360 |
| gatgagcagt tgaaatctgg aactgcctct gttgtgtgcc tgctgaataa cttctatccc | 420 |
| agagaggcca agtacagtgg aaggtggat aacgccctcc aatcgggtaa ctcccaggag | 480 | agtgtcacag agcaggacag caaggacagc acctacagcc tcagcagcac cctgacgctg    540 agcaaagcag actacgagaa acacaaagtc tacgcctgcg aagtcaccca tcagggcctg    600 agcttgcccg tcacaaagag cttgaacagg cgagagtgt                          639

<210> SEQ ID NO 12
<211> LENGTH: 321
<212> TYPE: DNA
<213> ORGANISM: Homo sapiens

<400> SEQUENCE: 12
gggcagcccc gagaaccaca ggtgtacacc ctgcccccat cccgggatga gctgaccaag     60
aaccaggtca gcctgacctg cctggtcaaa ggcttctatc ccagcgacat cgccgtggag    120
tgggagagca atgggcagcc ggagaacaac tacaagacca cgcctcccgt gctggactcc    180
gacggctcct tcttcctcta cagcaagctc accgtggaca agagcaggtg gcagcagggg    240
aacgtcttct catgctccgt gatgcatgag gctctgcaca accactacac gcagaagagc    300 ctctcccctgt ctccgggtaa a                                             321

<210> SEQ ID NO 13
<211> LENGTH: 321
<212> TYPE: DNA
<213> ORGANISM: Artificial Sequence
<220> FEATURE:
<223> OTHER INFORMATION: CH3 constant region of an anti-human-HER2
      antibody

<400> SEQUENCE: 13
gggcagcccc gagaaccaca ggtgtacacc ctgcccccat cccgggatga gctgaccaag     60
aaccaggtca gcctgtactg cctggtcaaa ggcttctatc ccagcgacat cgccgtggag    120
tgggagagca atgggcagcc ggagaacaac tacaagacca cgcctcccgt gctggactcc    180
gacggctcct tcttcctcta cagcaagctc accgtggaca agagcaggtg gcagcagggg    240
aacgtcttct catgctccgt gatgcatgag gctctgcaca accactacac gcagaagagc    300 ctctcccctgt ctccgggtaa a                                             321

<210> SEQ ID NO 14
<211> LENGTH: 321
<212> TYPE: DNA
<213> ORGANISM: Artificial Sequence
<220> FEATURE:
<223> OTHER INFORMATION: CH3 constant region of an anti-human-IGF-IR
      antibody

<400> SEQUENCE: 14
gggcagcccc gagaaccaca ggtgtacacc ctgcccccat cccgggatga gctgaccaag     60
aaccaggtca gcctgacctg cctggtcaaa ggcttctatc ccagcgacat cgccgtggag    120
tgggagagca atgggcagcc ggagaacaac tacaagacca cgcctcccgt gctggactcc    180
gacggctcct tcttcctcac cagcaagctc accgtggaca agagcaggtg gcagcagggg    240
aacgtcttct catgctccgt gatgcatgag gctctgcaca accactacac gcagaagagc    300 ctctcccctgt ctccgggtaa a                                             321

<210> SEQ ID NO 15
<211> LENGTH: 602
<212> TYPE: PRT
<213> ORGANISM: Homo sapiens

```
<400> SEQUENCE: 15

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Ser Glu Gln Phe Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415
```

-continued

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
            435                 440                 445

Thr Val Pro Trp Asp Gln Leu Phe Arg Asn Pro His Gln Ala Leu Leu
450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Ser Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
            515                 520                 525

His Cys Leu Pro Cys His Pro Glu Cys Gln Pro Gln Asn Gly Ser Val
            530                 535                 540

Thr Cys Phe Gly Pro Glu Ala Asp Gln Cys Val Ala Cys Ala Tyr Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His
            595                 600

<210> SEQ ID NO 16
<211> LENGTH: 907
<212> TYPE: PRT
<213> ORGANISM: Homo sapiens

<400> SEQUENCE: 16

Gly Glu Ile Cys Gly Pro Gly Ile Asp Ile Arg Asn Asp Tyr Gln Gln
1               5                   10                  15

Leu Lys Arg Leu Glu Asn Cys Thr Val Ile Glu Gly Tyr Leu His Ile
            20                  25                  30

Leu Leu Ile Ser Lys Ala Glu Asp Tyr Arg Ser Tyr Arg Phe Pro Lys
        35                  40                  45

Leu Thr Val Ile Thr Glu Tyr Leu Leu Leu Phe Arg Val Ala Gly Leu
    50                  55                  60

Glu Ser Leu Gly Asp Leu Phe Pro Asn Leu Thr Val Ile Arg Gly Trp
65                  70                  75                  80

Lys Leu Phe Tyr Asn Tyr Ala Leu Val Ile Phe Glu Met Thr Asn Leu
                85                  90                  95

Lys Asp Ile Gly Leu Tyr Asn Leu Arg Asn Ile Thr Arg Gly Ala Ile
            100                 105                 110

Arg Ile Glu Lys Asn Ala Asp Leu Cys Tyr Leu Ser Thr Val Asp Trp
        115                 120                 125

Ser Leu Ile Leu Asp Ala Val Ser Asn Asn Tyr Ile Val Gly Asn Lys
    130                 135                 140

Pro Pro Lys Glu Cys Gly Asp Leu Cys Pro Gly Thr Met Glu Glu Lys
145                 150                 155                 160

Pro Met Cys Glu Lys Thr Thr Ile Asn Asn Glu Tyr Asn Tyr Arg Cys
                165                 170                 175

Trp Thr Thr Asn Arg Cys Gln Lys Met Cys Pro Ser Thr Cys Gly Lys

```
                180                 185                 190
Arg Ala Cys Thr Glu Asn Asn Glu Cys Cys His Pro Glu Cys Leu Gly
            195                 200                 205

Ser Cys Ser Ala Pro Asp Asn Asp Thr Ala Cys Val Ala Cys Arg His
        210                 215                 220

Tyr Tyr Tyr Ala Gly Val Cys Val Pro Ala Cys Pro Pro Asn Thr Tyr
225                 230                 235                 240

Arg Phe Glu Gly Trp Arg Cys Val Asp Arg Asp Phe Cys Ala Asn Ile
                245                 250                 255

Leu Ser Ala Glu Ser Ser Asp Ser Glu Gly Phe Val Ile His Asp Gly
            260                 265                 270

Glu Cys Met Gln Glu Cys Pro Ser Gly Phe Ile Arg Asn Gly Ser Gln
        275                 280                 285

Ser Met Tyr Cys Ile Pro Cys Glu Gly Pro Cys Pro Lys Val Cys Glu
            290                 295                 300

Glu Glu Lys Lys Thr Lys Thr Ile Asp Ser Val Thr Ser Ala Gln Met
305                 310                 315                 320

Leu Gln Gly Cys Thr Ile Phe Lys Gly Asn Leu Leu Ile Asn Ile Arg
                325                 330                 335

Arg Gly Asn Asn Ile Ala Ser Glu Leu Glu Asn Phe Met Gly Leu Ile
            340                 345                 350

Glu Val Val Thr Gly Tyr Val Lys Ile Arg His Ser His Ala Leu Val
        355                 360                 365

Ser Leu Ser Phe Leu Lys Asn Leu Arg Leu Ile Leu Gly Glu Glu Gln
    370                 375                 380

Leu Glu Gly Asn Tyr Ser Phe Tyr Val Leu Asp Asn Gln Asn Leu Gln
385                 390                 395                 400

Gln Leu Trp Asp Trp Asp His Arg Asn Leu Thr Ile Lys Ala Gly Lys
                405                 410                 415

Met Tyr Phe Ala Phe Asn Pro Lys Leu Cys Val Ser Glu Ile Tyr Arg
            420                 425                 430

Met Glu Glu Val Thr Gly Thr Lys Gly Arg Gln Ser Lys Gly Asp Ile
        435                 440                 445

Asn Thr Arg Asn Asn Gly Glu Arg Ala Ser Cys Glu Ser Asp Val Leu
    450                 455                 460

His Phe Thr Ser Thr Thr Thr Ser Lys Asn Arg Ile Ile Ile Thr Trp
465                 470                 475                 480

His Arg Tyr Arg Pro Pro Asp Tyr Arg Asp Leu Ile Ser Phe Thr Val
                485                 490                 495

Tyr Tyr Lys Glu Ala Pro Phe Lys Asn Val Thr Glu Tyr Asp Gly Gln
            500                 505                 510

Asp Ala Cys Gly Ser Asn Ser Trp Asn Met Val Asp Val Asp Leu Pro
        515                 520                 525

Pro Asn Lys Asp Val Glu Pro Gly Ile Leu Leu His Gly Leu Lys Pro
    530                 535                 540

Trp Thr Gln Tyr Ala Val Tyr Val Lys Ala Val Thr Leu Thr Met Val
545                 550                 555                 560

Glu Asn Asp His Ile Arg Gly Ala Lys Ser Glu Ile Leu Tyr Ile Arg
                565                 570                 575

Thr Asn Ala Ser Val Pro Ser Ile Pro Leu Asp Val Leu Ser Ala Ser
            580                 585                 590

Asn Ser Ser Ser Gln Leu Ile Val Lys Trp Asn Pro Pro Ser Leu Pro
        595                 600                 605
```

-continued

Asn Gly Asn Leu Ser Tyr Tyr Ile Val Arg Trp Gln Arg Gln Pro Gln
            610                 615                 620

Asp Gly Tyr Leu Tyr Arg His Asn Tyr Cys Ser Lys Asp Lys Ile Pro
625                 630                 635                 640

Ile Arg Lys Tyr Ala Asp Gly Thr Ile Asp Ile Glu Glu Val Thr Glu
                645                 650                 655

Asn Pro Lys Thr Glu Val Cys Gly Gly Glu Lys Gly Pro Cys Cys Ala
            660                 665                 670

Cys Pro Lys Thr Glu Ala Glu Lys Gln Ala Glu Lys Glu Glu Ala Glu
            675                 680                 685

Tyr Arg Lys Val Phe Glu Asn Phe Leu His Asn Ser Ile Phe Val Pro
            690                 695                 700

Arg Pro Glu Arg Lys Arg Arg Asp Val Met Gln Val Ala Asn Thr Thr
705                 710                 715                 720

Met Ser Ser Arg Ser Arg Asn Thr Thr Ala Ala Asp Thr Tyr Asn Ile
                725                 730                 735

Thr Asp Pro Glu Glu Leu Glu Thr Glu Tyr Pro Phe Phe Glu Ser Arg
            740                 745                 750

Val Asp Asn Lys Glu Arg Thr Val Ile Ser Asn Leu Arg Pro Phe Thr
            755                 760                 765

Leu Tyr Arg Ile Asp Ile His Ser Cys Asn His Glu Ala Glu Lys Leu
770                 775                 780

Gly Cys Ser Ala Ser Asn Phe Val Phe Ala Arg Thr Met Pro Ala Glu
785                 790                 795                 800

Gly Ala Asp Asp Ile Pro Gly Pro Val Thr Trp Glu Pro Arg Pro Glu
                805                 810                 815

Asn Ser Ile Phe Leu Lys Trp Pro Glu Pro Glu Asn Pro Asn Gly Leu
            820                 825                 830

Ile Leu Met Tyr Glu Ile Lys Tyr Gly Ser Gln Val Glu Asp Gln Arg
            835                 840                 845

Glu Cys Val Ser Arg Gln Glu Tyr Arg Lys Tyr Gly Gly Ala Lys Leu
850                 855                 860

Asn Arg Leu Asn Pro Gly Asn Tyr Thr Ala Arg Ile Gln Ala Thr Ser
865                 870                 875                 880

Leu Ser Gly Asn Gly Ser Trp Thr Asp Pro Val Phe Phe Tyr Val Gln
                885                 890                 895

Ala Lys Thr Gly Tyr Glu Asn Phe Ile His Leu
            900                 905

<210> SEQ ID NO 17
<211> LENGTH: 29
<212> TYPE: DNA
<213> ORGANISM: Artificial Sequence
<220> FEATURE:
<223> OTHER INFORMATION: DNA Primer

<400> SEQUENCE: 17
ccaggtcagc ctgtactgcc tggtcaaag                                    29

<210> SEQ ID NO 18
<211> LENGTH: 29
<212> TYPE: DNA
<213> ORGANISM: Artificial Sequence
<220> FEATURE:
<223> OTHER INFORMATION: DNA Primer

<400> SEQUENCE: 18

```
ctttgaccag gcagtacagg ctgacctgg                                            29

<210> SEQ ID NO 19
<211> LENGTH: 29
<212> TYPE: DNA
<213> ORGANISM: Artificial Sequence
<220> FEATURE:
<223> OTHER INFORMATION: DNA Primer

<400> SEQUENCE: 19
ctccttcttc ctcaccagca agctcaccg                                            29

<210> SEQ ID NO 20
<211> LENGTH: 29
<212> TYPE: DNA
<213> ORGANISM: Artificial Sequence
<220> FEATURE:
<223> OTHER INFORMATION: DNA Primer

<400> SEQUENCE: 20
cggtgagctt gctggtgagg aagaaggag                                            29
```

ANTI-HER2 AND ANTI-IGF-IR BI-SPECIFIC ANTIBODIES AND USES THEREOF

CROSS-REFERENCE TO RELATED APPLICATIONS

This application claims benefit of U.S. Provisional Application No. 61/876,564, filed Sep. 11, 2013. Application No. 61/876,564, filed Sep. 11, 2013, is hereby incorporated herein by reference in its entirety.

REFERENCE TO SEQUENCE LISTING

The Sequence Listing submitted Sep. 11, 2014 as a text file named "UHK_00471_Sequence_Listing.txt," created on Sep. 11, 2014, and having a size of 38,031 bytes is hereby incorporated by reference pursuant to 37 C.F.R. §1.52(e)(5).

FIELD OF THE INVENTION

This disclosure pertains generally to potent bi-specific monoclonal antibodies against HER2 and IGF-IR, and methods of using the same for cancer therapy.

BACKGROUND OF THE INVENTION

Human Epidermal Growth Factor Receptor 2 (HER2), encoded by the ErbB2 gene, is a member of the epidermal growth factor receptor (EGFR/ErbB) family (Herbst, Int. J. Radiat. Oncol. Biol. Phys. 59:1-6 (2004)). HER2 is structurally similar to other EGFR family members, including HER1 (EGFR, ErbB1), HER3 (ErbB3), and HER4 (ErbB4), and also acts as a receptor tyrosine kinase. Homodimerization of HER1 and HER4 upon ligand binding activates intrinsic, intracellular protein-tyrosine kinase activity, resulting in receptor autophosphorylation and downstream signaling. These include signaling pathways such as the phosphatidylinositol 3-kinase (PI3K), the c-Jun NH(2)-terminal kinase (JNK), and the mitogen-activated protein kinase (MAPK), which promote DNA synthesis, cell proliferation, and inhibition of cell apoptosis. HER3 does not have a tyrosine kinase domain, so it transfers signals upon ligand binding through heterodimerization with other EGFR family members that have kinase activity.

Unlike HER1, HER3, and HER4, HER2 is unable to bind ligands and form homodimers. However, HER2 possesses tyrosine kinase activity, and appears to be the major signaling partner for EGFR family members through the formation of heteromeric complexes (Olayioye, Breast Cancer Res. 3:385-9 (2001)). Heterodimerization between two EGFR family members requires ligand binding (Spivak-Kroizman et al., J. Biol. Chem. 267:8056-63 (1992); Ferguson et al., Mol. Cell. Biol. 11:507-17 (2003)), but the crystal structure of a truncated HER2 ectodomain suggests that HER2 is constitutively in the activated conformation and readily interacting mostly with HER3 and other EGFR family members (Garrett et al., Mol. Cell. 11:495-505 (2003)). Overexpression of HER2 promotes ligand-independent formation of a HER2/HER3 receptor complex, a major oncogenic driver in HER2-overexpressing breast tumor cells (Stern, Sci. Transl. ed. 4:127rv2 (2012)). Cleavage of HER2 by the extracellular protease, ADAM10, produces the HER2 ectodomain and a truncated, constitutively active HER2 receptor (p95HER2) shown to drive carcinogenesis (Liu et al., Cancer Biol. Ther. 5:648-56 (2006)). HER2 overexpression is associated with strong activation of the PI3K pathway, which stimulates cell proliferation by activating the protein kinase Akt and down-regulating the cyclin-dependent kinase (CDK) inhibitor, p27 (Lane et al., Mol. Cell. Biol. 20:3210-23 (2000)). HER2 can also activate the MAPK pathway via interaction with SHC and GRB2 adaptor proteins (Dankort et al., J. Biol. Chem. 276:38921-8 (2001)). Overexpression of HER2 was found in breast and ovarian cancers, and associated with cancer metastasis (Abu Hejleh et al., World J. Gastrointest. Oncol. 4:103-8 (2012); Geng et al., Biomed. Pharmacother. 66:419-24 (2012); Nanni et al., PLoS One 7:e39626 (2012)), poor clinical outcome, and decreased survival rate (Ravdin and Chamness, Gene 159:19-27 (1995); Slamon et al., Science. 235: 177-82 (1987); Slamon et al., Science 244:707-12 (1989)).

Insulin-like Growth Factor Receptor type I (IGF-IR) is a tyrosine kinase receptor composed of two α subunits and two β subunits. Upon binding to either of the two ligands, Insulin-like growth factor I (IGF-I) or IGF-II, the extracellular domain of the α chains induces tyrosine autophosphorylation of the β chains in the cytoplasm. This activates the kinase activity of IGF-IR, and triggers downstream signaling via the PI3K/Akt and Ras/MAPK pathways, resulting in increased cell survival and cell proliferation (Jones and Clemmons, Endocrine reviews 16:3-34 (1995); LeRoith et al., Endocrine reviews 16:143-63 (1995)). Elevated IGF-IR is found in many tumor malignancies, including breast, prostate, and lung cancers (Warshamana-Greene et al., Clin. Cancer Res. 11:1563-71 (2005); Jones et al., Endocr. Relat. Cancer 11:793-814 (2004)). Additionally, overexpression of IGF-IR has been associated with disease progression and cancer metastasis (Krueckl et al., Cancer Res. 64:8620-9 (2004); Yao et al., N. Engl. J. Med. 357:39-51 (2007)).

HER2 is a widely used diagnostic marker and validated target for therapy. The humanized anti-HER2 mAb Herceptin (trastuzumab) has been effective in treating HER2-overexpressing breast cancers (Hudis, N. Engl. J. Med. 357:39-51 (2007); Tokunaga et al., Int. J. Clin. Oncol. 11:199-208 (2006)). Binding of Herceptin to HER2 causes internalization and degradation of the receptor in SKBR3 and MDA453 cells (Cuello et al., Cancer Res. 61:4892-900 (2001)). Herceptin binds to domain IV of the extracellular segment of HER2, leading to disruption of HER2/HER3 dimerization and ablation of downstream PI3K/Akt signaling (Stern, Sci. Transl. ed. 4:127rv2 (2012); Kute et al., Cytometry A. 57:86-93 (2004)). Herceptin can also inhibit cleavage of HER2 ectodomain in breast cancer cells, thus blocking the generation of a constitutively active truncated receptor (p95HER2) (Liu et al., Cancer Biol. Ther. 5:648-56 (2006); Albanell et al., Adv Exp Med. Biol. 532:253-68 (2003); Molina et al., Cancer Res. 61:4744-9 (2001)). In addition, Fc-mediated antibody-dependent cellular cytotoxicity (ADCC) may partially contribute to the anti-cancer activity of Herceptin in vivo (Clynes et al., Nat. Med. 6:443-6 (2000)).

Only 25-30% of breast cancer patients overexpress HER2, and patients treated with Herceptin can develop resistance as the disease progresses. Various mechanisms may account for this resistance, which likely involves the PI3K/Akt pathway, including elevated HER2-associated receptors and other receptors (Curr. Pharmacogenomics Person. Med. 7:263-74 (2009); Nahta et al., Nat. Clin. Pract. Oncol. 3:269-80 (2006)), cross activation between HER2 and other receptors (Yarden and Sliwkowski, Nat. Rev. Mol. Cell. Biol. 2:127-37 (2001); Huang et al., Cancer Res. 70:1204-14 (2010); Nahta et al., Cancer Res. 65:11118-28 (2005)), blockage of Herceptin by membrane-associated glycoproteins such as mucin-4, removal of the Herceptin epitope by cleavage, loss of HER2 expression, or increased HER2 expression. Accumulating evidence shows that crosstalk between HER2 and IGF-IR, including receptor heterodimerization and transactivation, and elevated IGF-IR signaling are associated with Herceptin resistance (Huang et al., Cancer Res. 70:1204-14 (2010); Jin and Esteva, J. Mammary Gland. Biol. Neoplasia 13:485-98 (2008); Bender and Nahta, Front. Biosci. 13:3906-12 (2008); Casa et al., Front. Biosci. 13:3273-87 (2008)).

Overexpression of IGF-IR in HER2-overexpressing breast cancer cell lines results in Herceptin resistance in vitro (Lu et al., J. Natl. Cancer Inst. 93:1852-7 (2001)). Inhibition of IGF-IR activity enhances the response to Herceptin in HER-2-positive breast cancer cells (Browne et al., Ann. Oncol. 22:68-73 (2011)). A phase II clinical trial of HER2-positive breast cancer patients revealed that overexpression of IGF-IR in the primary tumor was associated with resistance to Herceptin (Harris et al., Clin. Cancer Res. 13:1198-207 (2007)). We previously described a human/mouse chimeric mAb m590 that specifically bound with high affinity to IGF-IR and blocked the binding of IGF-I and IGF-II. This inhibited ligand-induced phosphorylation of IGF-IR in breast cancer MCF-7 cells (Zhang et al., MAbs. 1:475-80 (2009)).

BRIEF SUMMARY OF THE INVENTION

As described below, a bi-specific anti-HER2/anti-IGF-IR antibody was generated by engineering the m590 and Herceptin. It was found that co-targeting HER2 and IGF-IR with anti-HER2/anti-IGF-IR was more effective than targeting HER2 or IGF-IR alone by mono-specific antibodies in ablating tumor cell proliferation in vitro and in a SKOV-3 HER2- and IGF-IR-overexpressing breast cancer xenograft mouse model in vivo.

Disclosed are bi-specific antibodies that specifically bind to human Epidermal Growth Factor Receptor 2 (HER2) and human Insulin-like Growth Factor Receptor type I (IGF-IR). In certain embodiments, the bi-specific antibodies simultaneously bind to the extracellular domains of human HER2 and IGF-IR on cancer cells. In some embodiments, the bi-specific block binding of IGF-I and IGF-II to IGF-IR. In yet other embodiments they bind domain IV of the extracellular segment of HER2, disrupt dimerization of HER2 with HER3, ablate downstream PI3K/Akt signaling, inhibit cleavage of the HER2 ectodomain and generate a constitutively active truncated HER2 (p95HER2), and degrade HER2. Because the bi-specific anti-HER2/anti-IGF-IR antibody binds to HER2 and IGF-IR on the same cell, it can prevent HER2 antibody (Herceptin) resistance in HER2- and IGF-IR-overexpressing cancers.

In some embodiments, the isolated antibody (anti-HER2/anti-IGF-IR), or a binding fragment thereof, can comprise an amino acid sequence selected from Herceptin HC1 (SEQ ID NO: 1), Herceptin LC1 (SEQ ID NO: 2), m590 HC (SEQ ID NO: 3), m590 LC (SEQ ID NO: 4), and combinations thereof, wherein the antibody specifically binds to epitopes of HER2 and IGF-IR.

Also disclosed are pharmaceutical compositions comprising the disclosed antibody, epitopes that bind to the antibody, and methods of using the antibody to treat cancer in a mammal and to detect HER2 and IGF-IR in a mammal.

Additionally, the isolated nucleic acid molecule encoding the disclosed antibody, or a binding fragment thereof, can comprise a nucleic acid sequence selected from Herceptin HC1 DNA (SEQ ID NO: 8), Herceptin LC1 DNA (SEQ ID NO: 9), m590 HC DNA (SEQ ID NO: 10), m590 LC DNA (SEQ ID NO: 11), and combinations thereof, wherein the nucleic acid molecule is optionally in a form of a vector, wherein the nucleic acid molecule or vector is optionally contained within a host cell, wherein the antibody or binding fragment thereof specifically binds to epitopes of HER2 and IGF-IR. The disclosure also provides pharmaceutical compositions containing the nucleic acid molecules or polypeptides, and methods of using the nucleic acid molecules or polypeptides to inhibit cancer cell growth and cancer metastasis in a mammal.

To the accomplishment of the foregoing and related ends, the compounds, compositions, and methods can comprise the features hereinafter fully described and particularly pointed out in the claims. The following description and the annexed drawings set forth in detail certain illustrative aspects and implementations of the invention. These are indicative of, however, a few of the various ways in which the principles of the invention may be employed. Other objects, advantages, and novel features of the invention will become apparent from the following detailed description of the invention when considered in conjunction with the drawings.

BRIEF DESCRIPTION OF THE SEQUENCES

Figure 1:
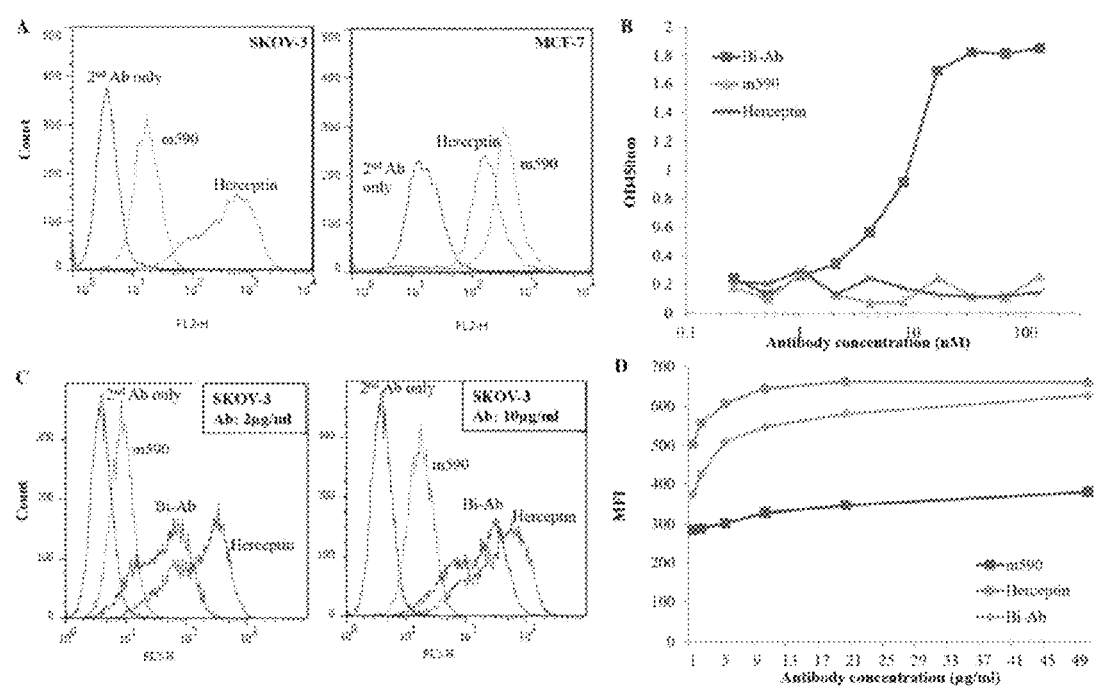
FIG. 1 shows a characterization of anti-HER2/anti-IGF-IR bi-specific antibodies for binding to recombinant HER2 and IGF-IR ectodomains and membrane-associated HER2 and IGF-IR in comparison with m590 and Herceptin. (A) Flow cytometry of MCF-7 breast cancer cells and SKOV-3 ovarian cancer cells stained with 10 µg/ml of m590 or Herceptin. (B) Simultaneous binding of anti-HER2/anti-IGF-IR to recombinant IGF-IR (coated) and HER2 ectodomains by indirect ELISA. (C) Binding of anti-HER2/anti-IGF-IR, m590 and Herceptin to membrane-associated IGF-IR and HER2 on SKOV-3 cells at 2 and 10 µg/ml of antibody concentration by flow cytometry. (D) Mean Fluorescence Intensity (MFI) of SKOV-3 cells stained with the antibodies at various concentrations.

SEQ ID NO: 1 is an amino acid sequence of the HC1 region of the Herceptin antibody (DrugBank DB00072 (BIOD00098, BTD00098; Heavy chain of Herceptin). Genomic DNA sequence of human IgG1 constant region is amino acids 121 to 449 of SEQ ID NO:1. CDR1 of the HC1 region is amino acids 28 to 35 of SEQ ID NO:1. CDR2 of the HC1 region is amino acids 50 to 59 of SEQ ID NO:1. CDR3 of the HC1 region is amino acids 99 to 109 of SEQ ID NO:1.

SEQ ID NO: 2 is an amino acid sequence of the LC1 region of the Herceptin antibody (DrugBank DB00072 (BIOD00098, BTD00098; Light chain of Herceptin). CDR1 of the LC1 region is amino acids 28 to 32 of SEQ ID NO:2. CDR2 of the LC1 region is amino acids 50 to 53 of SEQ ID NO:2. CDR3 of the LC1 region is amino acids 91 to 94 of SEQ ID NO:2.

SEQ ID NO: 3 is an amino acid sequence of the HC region of m590 antibody (Zhang M Y et al., MAbs 1: 475-80, 2009). Genomic DNA sequence of human IgG1 constant region is amino acids 127 to 455 of SEQ ID NO:3. CDR1 of the HC region is amino acids 26 to 33 of SEQ ID NO:3. CDR2 of the HC region is amino acids 51 to 58 of SEQ ID NO:3. CDR3 of the HC region is amino acids 97 to 112 of SEQ ID NO:3.

SEQ ID NO: 4 is an amino acid sequence of the LC region of m590 antibody (Zhang M Y et al., MAbs 1: 475-80, 2009). Human kappa light chain constant region is amino acids 108 to 213 of SEQ ID NO:4. CDR1 of the LC region is amino acids 27 to 31 of SEQ ID NO:4. CDR2 of the LC region is amino acids 49 to 51 of SEQ ID NO:4. CDR3 of the LC region is amino acids 88 to 96 of SEQ ID NO:4.

SEQ ID NO: 5 is an amino acid sequence of a human CH3 constant region.

SEQ ID NO: 6 is an amino acid sequence of a CH3 constant region of an anti-human-HER2 antibody, wherein the CH3 constant region contains a T366Y mutation. The mutation is at amino acid 26 in SEQ ID NO:6.

SEQ ID NO: 7 is an amino acid sequence of a CH3 constant region of an anti-human-IGF-IR antibody, wherein the CH3 constant region contains a Y407T mutation. The mutation is at amino acid 67 in SEQ ID NO:7.

SEQ ID NO: 8 is a nucleic acid sequence encoding the HC1 region of the Herceptin antibody (DrugBank DB00072 (BIOD00098, BTD00098; Heavy chain of Herceptin). Genomic DNA sequence of human IgG1 constant region is nucleotides 360 to 1957 of SEQ ID NO:8. Sequence encoding the CH1 is nucleotides 361 to 651 of SEQ ID NO:8. Sequence encoding the hinge region is nucleotides 1045 to 1089 of SEQ ID NO:8. Sequence encoding the CH2 is nucleotides 1208 to 1537 of SEQ ID NO:8. Sequence encoding the CH3 is nucleotides 1634 to 1954 of SEQ ID NO:8. Stop codon is nucleotides 1955 to 1957 of SEQ ID NO:8.

SEQ ID NO: 9 is a nucleic acid sequence encoding the LC1 region of the Herceptin antibody (DrugBank DB00072 (BIOD00098, BTD00098; Light chain of Herceptin). Stop codon is nucleotides 643 to 645 of SEQ ID NO:9.

SEQ ID NO: 10 is a nucleic acid sequence encoding the HC region of m590 antibody (Zhang M Y et al., MAbs 1: 475-80, 2009). Genomic DNA sequence of human IgG1 constant region is nucleotides 378 to 1975 of SEQ ID NO:10. Sequence encoding the CH1 is nucleotides 379 to 669 of SEQ ID NO:10. Sequence encoding the hinge region is nucleotides 1063 to 1107 of SEQ ID NO:10. Sequence encoding the CH2 is nucleotides 1226 to 1555 of SEQ ID NO:10. Sequence encoding the CH3 is nucleotides 1652 to 1972 of SEQ ID NO:10. Stop codon is nucleotides 1973 to 1975 of SEQ ID NO:10.

SEQ ID NO: 11 is a nucleic acid sequence encoding the LC region of m590 antibody (Zhang M Y et al., MAbs 1: 475-80, 2009). Human kappa light chain constant region is encoded by nucleotides 322 to 639 of SEQ ID NO:11.

SEQ ID NO: 12 is a nucleic acid sequence encoding a human CH3 constant region2.

SEQ ID NO: 13 is a nucleic acid sequence encoding a CH3 constant region of an anti-human-HER2 antibody, wherein the CH3 constant region contains a T366Y mutation. The mutant codon is at nucleotides 76 to 78 in SEQ ID NO:13.

SEQ ID NO: 14 is a nucleic acid sequence encoding a CH3 constant region of an anti-human-IGF-IR antibody, wherein the CH3 constant region contains a Y407T mutation. The mutant codon is at nucleotides 199 to 201 in SEQ ID NO:14.

SEQ ID NO: 15 is the amino acid sequence of the human HER2 (GenBank Accession No. P04626; GI 119533).

SEQ ID NO: 16 is the amino acid sequence of the human IGF-IR (GenBank Accession No. P08069; GI 124240).

SEQ ID NO: 17 is a forward primer used for the T366Y mutagenesis of pDR12-Herceptin or pDR12-m590.

SEQ ID NO: 18 is a reverse primer used for the T366Y mutagenesis of pDR12-Herceptin or pDR12-m590.

SEQ ID NO: 19 is a forward primer used for the Y407T mutagenesis pDR12-m590 or pDR12-Herceptin.

SEQ ID NO: 20 is a reverse primer used for the Y407T mutagenesis pDR12-m590 or pDR12-Herceptin.

DETAILED DISCLOSURE OF THE INVENTION

Patients treated with the humanized anti-HER2 antibody Herceptin can develop resistance as the disease progresses. Accumulating evidence shows that crosstalk between HER2 and IGF-IR, including receptor heterodimerization and transactivation, and elevated IGF-IR signaling are associated with Herceptin resistance (Huang et al., Cancer Res. 70:1204-14 (2010); Jin and Esteva, J. Mammary Gland. Biol. Neoplasia 13:485-98 (2008); Bender and Nahta, Front. Biosci. 13:3906-12 (2008); Casa et al., Front. Biosci. 13:3273-87 (2008)).

Disclosed are bi-specific antibodies or fragments thereof that bind to an epitope of human epidermal growth factor receptor 2 (HER2) and an epitope of the type 1 insulin-like growth factor receptor (IGF-IR). The disclosure more specifically provides antibodies or fragments thereof which bind to the extracellular domain of HER2 (such as human HER2) and the extracellular domain of IGF-IR (such as human IGF-IR). Advantageously, the disclosed antibodies significantly inhibit growth of HER2/IGF-IR-expressing cancer cells. Additionally, disclosed are epitopes that are recognized by the polypeptides (e.g. antibodies or binding fragments thereof) described herein, which epitopes can be used in the development of anti-HER2/anti-IGF-IR bi-specific antibodies for the treatment of cancer.

The anti-HER2/anti-IGF-IR bi-specific antibodies can be used for cancer therapy, as well as to detect HER2 and IGF-IR in an animal, including without limitation a human.

The disclosed anti-HER2/anti-IGF-IR antibodies can also be used to detect HER2 and IGF-IR in a test sample. The test sample can be a tissue sample, a biopsy sample, and the like.

In some embodiments, the anti-HER2/anti-IGF-IR antibody specifically binds to human epidermal growth factor receptor 2 (HER2) and human insulin-like growth factor I receptor (also known as human insulin-like growth factor receptor type 1 (IGF-IR)). In some embodiments, the human HER2 has an amino acid sequence of SEQ ID NO: 15 (GenBank Accession No. P04626; GI 119533) and the human IGF-IR has an amino acid sequence of SEQ ID NO: 16 (GenBank Accession No. P08069; GI: 124240). In some embodiments, the disclosed anti-HER2/anti-IGF-IR antibody specifically binds to human HER2 and human IGF-IR expressed on cancer cells, such as for example, SKOV-3 and MCF-7 cells. In some embodiments, the disclosed anti-HER2/anti-IGF-IR antibody specifically binds to human HER2 and human IGF-IR expressed on SKOV-3 cells in a xenograft mouse model.

Also disclosed is the use of the "knobs-into-holes" approach to generate an anti-HER2/anti-IGF-IR hybrid IgG described by Ridgway et al., Protein Eng. 9: 671-21, (1996), which is hereby incorporated by reference. A "knob" mutant can be created by replacing a Threonine with Tyrosine (T366Y) in the CH3 domain of anti-HER2 antibody (such as Herceptin) or anti-IGF-IR antibody (such as m590). A "hole" mutant can be made by replacing a Tyrosine with Threonine (Y407T) in the CH3 domain of anti-IGF-IR antibody (such as m590) or anti-HER2 antibody (such as Herceptin). Also disclosed is the co-transfection of a human cell, for example 293F cell or hybridoma cell, with the "knob" and "hole" plasmids which results in the production of stable heterodimers that exhibit bi-specificity for both HER2 and IGF-IR.

The term "binding specificity," "specificity," "specifically reacts," or "specifically interacts," as used herein, refers to the ability of an antibody or other agent to detectably bind an epitope presented on an antigen, such as epitopes of HER2 and IGF-IR, while having relatively little detectable reactivity with other proteins or structures. Specificity can be relatively determined by binding or competitive assays, using e.g., Biacore instruments. Specificity can be exhibited by, e.g., an about 10:1, about 20:1, about 50:1, about 100:1, about 10,000:1 or greater ratio of affinity/avidity in binding to the specific antigen versus nonspecific binding to other irrelevant molecules. In the context of the disclosed antibodies and polypeptides, "bi-specific" and similar terms refer to antibodies or polypeptides containing at least two different specific binding elements that each specifically binds to a different epitope or ligand.

Also disclosed are methods for generating anti-HER2/anti-IGF-IR antibodies, or fragments thereof. Anti-HER2/anti-IGF-IR bi-specific hybrid IgG antibodies can be generated by combining (1) the heavy chain 1 (HC1) and light chain 1 (LC1) of humanized Herceptin [DrugBank: Trastuzumab (DB00072) (BIOD00098, BTD00098)] and (2) the HC and LC of anti-IGF-IR mouse/human chimeric antibody (m590) described in U.S. Pat. No. 8,444,982 and Zhang et al., Mabs 1:5, 475-480 (2009), both of which are hereby incorporated by reference.

In some embodiments, the disclosed isolated polypeptide (e.g., antibody, or a binding fragment thereof), or the polypeptide or fragment thereof binds to an epitope of HER2 and IGF-IR ectodomains. In certain embodiments, the isolated polypeptide can comprise the amino acid sequence selected from Herceptin HC1 (SEQ ID NO: 1), Herceptin LC1 (SEQ ID NO: 2), m590 HC (SEQ ID NO: 3), m590 LC (SEQ ID NO: 4), and fragments thereof. In some embodiments, the CH3 constant region of the anti-HER2/anti-IGF-IR antibody comprises SEQ ID NO: 5. In some embodiments, the CH3 constant region containing a T366Y mutation comprises SEQ ID NO: 6. In some embodiments, the CH3 constant region containing a Y407T mutation comprises SEQ ID NO: 7.

The disclosure also provides an isolated nucleic acid molecule encoding a polypeptide, or a binding fragment thereof. In certain embodiments, the nucleic acid molecule can comprise Herceptin HC1 DNA (SEQ ID NO: 8), Herceptin LC1 DNA (SEQ ID NO: 9), m590 HC DNA (SEQ ID NO: 10), m590 LC DNA (SEQ ID NO: 11), CH3 constant region DNA (SEQ ID NO: 12), DNA encoding a CH3 constant region containing a T366Y mutation (SEQ ID NO: 13), DNA encoding a CH3 constant region containing a Y407T mutation (SEQ ID NO: 14), and fragments thereof. In certain embodiments, the nucleic acid molecule is optionally in the form of a vector, wherein the nucleic acid molecule or vector is optionally contained within a host cell. In certain embodiments, the anti-HER2 and anti-IGF-IR bi-specific antibodies, as well as nucleic acid molecules encoding the bi-specific antibodies, can use a "knob-into-holes" strategy to engineer CH3 for heterodimerization. For bi-specific antibodies, knob(s) can be created by replacing small amino acid side chains with larger amino acids at the interface between one CH3 domain, whereas hole(s) can be created by replacing large side chains with small amino acids in the partner CH3 domain.

In certain embodiments, the anti-HER2 and anti-IGF-IR bi-specific antibodies, as well as nucleic acid molecules encoding the bi-specific antibodies, can contain a "knob" T366Y mutation in the CH3 domain of the anti-HER2 antibody, and the bi-specific antibody can contain a "hole" Y407T mutation in the CH3 domain of the anti-IGF-IR antibody.

In certain embodiments, the anti-HER2 and anti-IGF-IR bi-specific antibodies, as well as nucleic acid molecules encoding the bi-specific antibodies, can contain a "knob" T366Y mutation in the CH3 domain of the anti-IGF-IR antibody, and the bi-specific antibody can contain a "hole" Y407T mutation in the CH3 domain of the anti-HER2 antibody.

The polypeptide can be any suitable polypeptide. For example, in some embodiments, the polypeptide is an antibody. Antibodies include both polyclonal and monoclonal antibodies. In addition to intact immunoglobulin molecules, also included are fragments or polymers of those immunoglobulin molecules, and human or humanized versions of immunoglobulin molecules or fragments thereof, as long as the molecules maintain the ability to bind with an epitope of the HER2 and IGF-IR. The antibodies can be tested for their desired activity using the in vitro assays described herein, or by analogous methods, after which their in vivo therapeutic and/or diagnostic activities can be confirmed and quantified according to known clinical testing methods.

In some embodiments, the polypeptide is a monoclonal antibody or a binding fragment thereof. A monoclonal antibody refers to an antibody where individual antibodies within a population are identical.

The term "polypeptide" encompasses native or artificial proteins, protein fragments and polypeptide analogs of a protein sequence. A polypeptide may be monomeric or polymeric. The term "isolated polypeptide" is a polypeptide that by virtue of its origin or source of derivation (1) is not associated with naturally associated components that accompany it in its native state, (2) is substantially free of other proteins from the same species, (3) is expressed by a cell of a species different from where the protein naturally originates, or (4) does not occur in nature. A polypeptide that is chemically synthesized or synthesized in a cellular system different from the cell from which it naturally originates is also considered "isolated" from its naturally associated components. A polypeptide can also be rendered substantially free of naturally associated components by isolation, using purification techniques well known in the art. Similar definitions apply to antibodies with analogous meaning.

Native antibodies are usually heterotetrameric glycoproteins, composed of two identical light chains (LC) and two identical heavy chains (HC). LC Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H) or $V_H$) followed by a number of constant domains. Each light chain has a variable domain at one end (V(L) or $V_L$) and a constant domain at its other end; the constant domain of the light chain is aligned with the first constant domain of the heavy chain, and the light chain variable domain is aligned with the variable domain of the heavy chain. Particular amino acid residues are understood to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

In the context of antibodies, fragments thereof, and the disclosed polypeptides, the terms "variable region," "variable sequence," and the like, are used to describe certain portions of the variable domains that differ in sequence among antibodies and are used in the binding and specificity of each particular antibody for its particular antigen. However, the variability is not evenly distributed through the variable domains of antibodies. It is typically concentrated in three segments called complementarity determining regions (CDRs) or hypervariable (HV) regions both in the light chain and the heavy chain variable domains. The more highly conserved portions of the variable domains are called the framework (FR). The variable domains of native heavy and light chains each comprise four FR regions FR1, FR2, FR3, and FR4, largely adopting a β-sheet configuration, connected by three CDRs (HV1, HV2, HV3), which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). CRDs are typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain (Kabat et al., *Sequences of Proteins of Immunological Interest,* 5th Ed. Public Health Service, National Institutes of Health, Bethesda, Md. (1991)). Residues that form core "hypervariable loops" are typically at approximately residues 26-32 (L1), 50-52 (L2) and 91-96 (L3) in the light chain variable domain and 26-32 (H1), 53-55 (H2) and 96-101 (H3) in the heavy chain variable domain (Chothia and Lesk, 1987, J. Mol. Biol. 196:901-917). The constant domains are not involved directly in binding an antibody to an antigen, but exhibit various effector functions, such as participation of the antibody in antibody-dependent cellular toxicity.

It is well-known that the variable regions of antibodies—and, in particular, the complementarity determining regions (CDRs) of the variable regions—are primarily responsible for the binding and binding specificity of antibodies. It is also well-known that portions of antibodies other than the variable regions (or other than the CDRs) can be substituted, altered, eliminated, etc. without abolishing the binding and binding specificity of the antibodies (or antibody fragments in the case of elimination of portions of the antibody). The well-known modular nature of antibody structure allows extensive substitution, alteration, elimination, etc. of portions of antibodies other than the variable regions (or other than the CDRs) while retaining the binding and binding specificity of the variable regions and CDRs. For example, the disclosed antibodies, antibody fragments, and peptides can be can comprise any form of antibody binding fragments that contains the CDR sequences of Herceptin and any form of antibody binding fragments that contains the CDR sequences of m590. Such principals have been amply demonstrated by production and use of chimeric antibodies, recombinant antibodies, humanized antibodies, and the numerous types of antibody fragments and antibody-derived polypeptides, such as $F(ab')_2$, fragment antigen-binding (Fab), half antibodies, single-chain variable fragments (scFv), VhH domain, V-NAR domain, $V_H$ domain, $V_L$ domain, $F(ab)_3$, bis-scFv, diabody, triabody, tetrabody, and minibody (Hollinger and Hudson, Nature Biotech. 23(9): 1126-1136 (2005)(and references cited therein), Holliger & Winter, Proc. Natl. Acad. Sci. USA 90, 6444-6448 (1993); Pei et al., Proc. Natl. Acad. Sci. USA 94, 9637-9642 (1997); Iliades et al., FEBS Lett. 409, 437-441 (1997); De Genst et al., J. Biol. Chem. 280, 14114-14121 (2005); De Genst et al., J. Biol. Chem. 279, 53593-53601 (2004); Dooley & Flajnik, Eur. J. Immunol. 35, 936-945 (2005); Streltsov & Nuttall, Immunol. Lett. 97, 159-160 (2005); Streltsov et al., Proc. Natl. Acad. Sci. USA 101, 12444-12449 (2004); Cortez-Retamozo et al., Cancer Res. 64, 2853-2857 (2004); Dottorini et al., Biochemistry 43, 622-628 (2004); Colby et al., J. Mol. Biol. 342, 901-912 (2004); Jespers et al., J. Mol. Biol. 337, 893-903 (2004); Linsley, Nat. Immunol. 6, 231-232 (2005); 37. Casey et al., Br. J. Cancer 86, 1401-1410 (2002); Weir et al., Biochem. Soc. Trans. 30, 512-516 (2002); Dolezal et al., Protein Eng. 16, 47-56 (2003); Power et al., Methods Mol. Biol. 207, 335-350 (2003); Arndt et al., FEBS Lett. 578, 257-261 (2004); Griffiths et al., J. Nucl. Med. 45, 30-39 (2004); Olafsen et al., Protein Eng. Des. Sel. 17, 21-27 (2004); Wittel et al., Nucl. Med. Biol. 32, 157-164 (2005); Le Gall et al., Protein Eng. Des. Sel. 17, 357-366 (2004); Kenanova et al., Cancer Res. 65, 622-631 (2005); Adams et al., Cancer Res. 64, 6200-6206 (2004); Grosse-Hovest et al., Int. J. Cancer; published online 7 Jul. 2005 (interscience.wiley.com/cgi-bin/abstract/110559371/AB-STRACT 120); Holliger et al., Cancer Res. 59, 2909-2916 (1999); Pattersen et al., J. Comput. Chem. 25, 1605-1612 (2004); Olafsen et al., Cancer Res. 65, 5907-5916 (2005); Shen et al., J. Nucl. Med. 46, 642-651 (2005); Nellis et al., Biotechnol. Prog. 21, 221-232 (2005); Ebbinghaus et al., Int. J. Cancer 116, 304-313 (2005); Wong et al., Clin. Cancer Res. 10, 5014-5021 (2004); Hulstein et al., Blood; published online 12 Jul. 2005 (bloodjournal.org/cgi/reprint/2005-03-1153v1)).

Thus, embodiments of the disclosed antibodies and polypeptides that use the binding and binding specificity of the antibody (and do not require a particular biological function of the antibody constant regions) can comprise a binding fragment specific for HER2 and binding fragment specific for IGF-IR. For antibody forms of the disclosed antibodies and polypeptides, the other antibody regions can be substituted, altered, or both, with or from any heavy and light chains or portions thereof, with the expectation that the bi-specific binding and binding specificity for HER2 and IGF-IR will be retained. For antibody fragment and peptide forms, the binding fragment specific for HER2 and the binding fragment specific for IGF-IR can be embodied by any of numerous binding fragment forms and can be linked in any suitable way, including in any of the multivalent and multi-specific ways used for antibody binding fragments. In the case of the disclosed antibodies, antibody fragments, and polypeptides, such forms will be bi-specific instead of (or in addition to) multivalent. Examples of binding fragment forms include F(ab')$_2$, fragment antigen-binding (Fab), half antibodies, single-chain variable fragments (scFv), VhH domain, V-NAR domain, $V_H$ domain, $V_L$ domain, F(ab)$_3$, bis-scFv, diabody, triabody, tetrabody, and minibody. Any of these forms can be independently used to embody the binding fragment specific for HER2 and the binding fragment specific for IGF-IR and then can be combined or joined using any suitable linker or coupling. The binding fragment specific for HER2 and the binding fragment specific for IGF-IR can also each be used as a binding fragment portion of a multivalent and/or multi-specific form of antibody fragments. Examples include F(ab')$_2$, F(ab)$_3$, bis-scFv, diabody, triabody, tetrabody, and minibody.

As used herein, the terms "binding fragment," "antigen binding fragment," "antibody binding fragment," and the like, refer to one or more portions of an antibody that contain the antibody's CDRs and, optionally, the framework residues that comprise the antibody's "variable region" antigen recognition site, and exhibit an ability to immunospecifically bind antigen. Such fragments include Fab', F(ab')2, Fv, single chain (ScFv), etc., and mutants and variants thereof, naturally occurring variants. As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As discussed in detail herein, the variable regions can also be substituted and altered in ways that do not eliminate the binding and binding specificity of the variable region or CDRs. For the disclosed antibodies and polypeptides with substitutions, alterations, eliminations, etc. of portions of antibodies other than the variable regions (or other than the CDRs), it is preferred that the variable region sequences and the CDR sequences are, or are modeled after, the variable regions or CDRs of Herceptin and m590 antibodies.

The disclosure encompasses chimeric antibodies and hybrid antibodies, with dual or multiple antigen or epitope specificities, and fragments, such as F(ab')2 and the like, including hybrid fragments. Such antibodies and fragments can be made by techniques known in the art and can be screened for specificity and activity according to general methods for producing antibodies and screening antibodies for specificity and activity (see, e.g., Harlow and Lane. Antibodies, A Laboratory Manual. Cold Spring Harbor Publications, New York, (1988), which is hereby incorporated by reference).

The disclosure also encompasses human antibodies and/or humanized antibodies. Many non-human antibodies (e.g., those derived from mice, rats, or rabbits) are naturally antigenic in humans and, thus, can give rise to undesirable immune responses when administered to humans. Therefore, the use of human or humanized antibodies in the methods described herein serves to lessen the chance that an antibody administered to a human will evoke an undesirable immune response.

The human antibodies and humanized antibodies described herein can be prepared by any known technique. Examples of techniques for human monoclonal antibody production include those described by Boerner et al., J. Immunol., 147(1), 86-95 (1991), which is hereby incorporated by reference. Human antibodies described herein (and fragments thereof) can also be produced using phage display libraries (see, e.g., Marks et al., J. Mol. Biol., 222, 581-597 (1991)), which is hereby incorporated by reference. The human antibodies described herein can also be obtained from transgenic animals. For example, transgenic mutant mice that are capable of producing a full repertoire of human antibodies in response to immunization have been described (see, e.g., Jakobovits et al., PNAS, 90, 2551-255 (1993); and Jakobovits et al., Nature, 362, 255-258 (1993)), all of which are hereby incorporated by reference.

Methods for humanizing non-human antibodies are known in the art. For example, humanized antibodies can be generated by substituting rodent complementarity-determining regions (CDRs) or CDR sequences for the corresponding sequences of a human antibody. Detailed procedures are disclosed in Jones et al., Nature, 321, 522-525 (1986); Riechmann et al., Nature, 332, 323-327 (1988); Verhoeyen et al., Science, 239, 1534-1536 (1988), all of which are hereby incorporated by reference.

Methods that can be used to produce humanized antibodies are also described in U.S. Pat. No. 4,816,567; U.S. Pat. No. 5,565,332; U.S. Pat. No. 5,721,367; U.S. Pat. No. 5,837,243; U.S. Pat. No. 5,939,598; U.S. Pat. No. 6,130,364; and U.S. Pat. No. 6,180,377; all of which are hereby incorporated by reference.

Human, chimeric, or humanized derivatives of anti-human HER2 and/or IGF-IR antibodies are particularly preferred for in vivo use in humans, however, murine antibodies or antibodies of other species may be advantageously employed for many uses (for example, in vitro or in situ detection assays, acute in vivo use, etc.). A humanized antibody can comprise amino acid residue substitutions, deletions or additions in one or more non-human CDRs. The humanized antibody derivative may have substantially the same binding, stronger binding or weaker binding when compared to a non-derivative humanized antibody. In specific embodiments, one, two, three, four, or five amino acid residues of the CDR have been substituted, deleted or added (i.e., mutated). Completely human antibodies are particularly desirable for therapeutic treatment of human subjects.

Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a HER2 and/or IGF-IR polypeptide. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

A "chimeric antibody" is a molecule in which different portions of the antibody are derived from different immunoglobulin molecules such as antibodies having a variable region derived from a non-human antibody and a human immunoglobulin constant region. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807,715, 4,816,567, and 4,816,397. Chimeric antibodies comprising one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519,596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332).

Of particular interest are "humanized antibodies" (see, e.g., European Patent Nos. EP 239,400, EP 592,106, and EP 519,596; International Publication Nos. WO 91/09967 and WO 93/17105; U.S. Pat. Nos. 5,225,539, 5,530,101, 5,565,332, 5,585,089, 5,766,886, and 6,407,213; and Padlan, 1991, Molecular Immunology 28(4/5):489-498; Studnicka et al., 1994, Protein Engineering 7(6):805-814; Roguska et al., 1994, PNAS 91:969-973; Tan et al., 2002, J. Immunol. 169:1119-1125; Caldas et al., 2000, Protein Eng. 13:353-360; Morea et al., 2000, Methods 20:267-79; Baca et al., 1997, J. Biol. Chem. 272:10678-10684; Roguska et al., 1996, Protein Eng. 9:895-904; Couto et al., 1995, Cancer Res. 55 (23 Supp):5973s-5977s; Couto et al., 1995, Cancer Res. 55:1717-22; Sandhu, 1994, Gene 150:409-10; Pedersen et al., 1994, J. Mol. Biol. 235:959-973; Jones et al., 1986, Nature 321:522-525; Reichmann et al., 1988, Nature 332:323-329; and Presta, 1992, Curr. Op. Struct. Biol. 2:593-596). As used herein, the term "humanized antibody" refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A humanized antibody is an antibody comprising a humanized light chain and a humanized heavy chain immunoglobulin. For example, a humanized antibody would not encompass a typical chimeric antibody, because, e.g., the entire variable region of a chimeric antibody is non-human. One says that the donor antibody has been "humanized," by the process of "humanization," because the resultant humanized antibody is expected to bind to the same antigen as the donor antibody that provides the CDR's. For the most part, humanized antibodies are human immunoglobulins (recipient antibody) in which hypervariable region residues of the recipient are replaced by hypervariable region residues from a non-human species (donor antibody) such as mouse, rat, rabbit or a non-human primate having the desired specificity, affinity, and capacity. In some instances, Framework Region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin that immunospecifically binds to an FcγRIIB polypeptide, that has been altered by the introduction of amino acid residue substitutions, deletions or additions (i.e., mutations).

DNA sequences coding for preferred human acceptor framework sequences include but are not limited to FR segments from the human germline VH segment VH1-18 and JH6 and the human germline VL segment VK-A26 and JK4. In a specific embodiment, one or more of the CDRs are inserted within framework regions using routine recombinant DNA techniques. The framework regions may be naturally occurring or consensus framework regions, and preferably human framework regions (see, e.g., Chothia et al., 1998, "Structural Determinants In The Sequences Of Immunoglobulin Variable Domain," J. Mol. Biol. 278: 457-479 for a listing of human framework regions).

A humanized or chimeric HER2 and/or IGF-IR antibody can include substantially all of at least one, and typically two, variable domains in which all or substantially all of the CDR regions correspond to those of a non-human immunoglobulin (i.e., donor antibody) and all or substantially all of the framework regions are those of a human immunoglobulin consensus sequence. Preferably, a HER2 and/or IGF-IR antibody also includes at least a portion of an immunoglobulin constant region (Fc), typically that of a human immunoglobulin. The constant domains of the HER2 and/or IGF-IR antibodies may be selected with respect to the proposed function of the antibody, in particular the effector function which may be required. In some embodiments, the constant domains of the HER2 and/or IGF-IR antibodies are (or comprise) human IgA, IgD, IgE, IgG or IgM domains. In a specific embodiment, human IgG constant domains, especially of the IgG1 and IgG3 isotypes are used, when the humanized HER2 and/or IGF-IR antibodies is intended for therapeutic uses and antibody effector functions such as antibody-dependent cell-mediated cytotoxicity (ADCC) and complement-dependent cytotoxicity (CDC) activity are needed. In alternative embodiments, IgG2 and IgG4 isotypes are used when the HER2 and/or IGF-IR antibody is intended for therapeutic purposes and antibody effector function is not required. The invention encompasses Fc constant domains comprising one or more amino acid modifications which alter antibody effector functions such as those disclosed in U.S. Patent Application Publication Nos. 2005/0037000 and 2005/0064514.

In some embodiments, the HER2 and/or IGF-IR antibody contains both the light chain as well as at least the variable domain of a heavy chain. In other embodiments, the HER2 and/or IGF-IR antibody may further include one or more of the CH1, hinge, CH2, CH3, and CH4 regions of the heavy chain. The antibody can be selected from any class of immunoglobulins, including IgM, IgG, IgD, IgA and IgE, and any isotype, including IgG1, IgG2, IgG3 and IgG4. In some embodiments, the constant domain is a complement fixing constant domain where it is desired that the antibody exhibit cytotoxic activity, and the class is typically IgG1. In other embodiments, where such cytotoxic activity is not desirable, the constant domain may be of the IgG2 class. The HER2 and/or IGF-IR antibody may comprise sequences from more than one class or isotype, and selecting particular constant domains to optimize desired effector functions is within the ordinary skill in the art.

The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the donor antibody. Such mutations, however, are preferably not extensive. Usually, at least 75% of the humanized antibody residues will correspond to those of the parental framework region (FR) and CDR sequences, more often 90%, and most preferably greater than 95%. Humanized antibodies can be produced using variety of techniques known in the art, including, but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, Proc. Natl. Acad. Sci. 91:969-973), chain shuffling (U.S. Pat. No. 5,565,332), and techniques disclosed in, e.g., U.S. Pat. Nos. 6,407,213, 5,766,886, 5,585,089, International Publication No. WO 9317105, Tan et al., 2002, J. Immunol. 169:1119-25, Caldas et al., 2000, Protein Eng. 13:353-60, Morea et al., 2000, Methods 20:267-79, Baca et al., 1997, J. Biol. Chem. 272:10678-84, Roguska et al., 1996, Protein Eng. 9:895-904, Couto et al., 1995, Cancer Res. 55 (23 Supp):5973s-5977s, Couto et al., 1995, Cancer Res. 55:1717-22, Sandhu, 1994, Gene 150:409-10, Pedersen et al., 1994, J. Mol. Biol. 235:959-73, Jones et al., 1986, Nature 321:522-525, Riechmann et al., 1988, Nature 332:323, and Presta, 1992, Curr. Op. Struct. Biol. 2:593-596. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; U.S. Publication Nos. 2004/0049014 and 2003/0229208; U.S. Pat. Nos. 6,350,861; 6,180,370; 5,693,762; 5,693,761; 5,585,089; and 5,530,101 and Riechmann et al., 1988, Nature 332:323).

The monoclonal antibodies can be made using any procedure known in the art. For example, the monoclonal antibodies can be made by recombinant DNA methods, such as those described in U.S. Pat. No. 4,816,567, which is hereby incorporated by reference. DNA encoding the disclosed monoclonal antibodies can be readily isolated and sequenced using conventional procedures (e.g., by using oligonucleotide probes that are capable of binding specifically to genes encoding the heavy and light chains of antibodies). Libraries of antibodies or active antibody fragments can also be generated and screened using phage display techniques, e.g., as described in U.S. Pat. No. 5,804,440 and U.S. Pat. No. 6,096,441, both of which are hereby incorporated by reference. Monoclonal antibodies can also be prepared using hybridoma methods, such as those described by Kohler et al., Nature, 256, 495-497 (1975), which is hereby incorporated by reference.

The disclosed antibodies, fragments, and polypeptides generally are multi-specific. Of interest are bi-specific antibodies, fragments, and polypeptides, tri-specific antibodies, fragments, and polypeptides, and antibodies, fragments, and polypeptides of greater multi-specificity that exhibit specificity to different targets in addition to HER2 and IGF-IR, such as other molecules of the immune system. For example, such antibodies can bind to both HER2 and IGF-IR and to an antigen that is important for targeting the antibody to a particular cell type or tissue (for example, to an antigen associated with a cancer antigen of a tumor being treated).

In some embodiments, such multi-specific antibody binds to molecules (receptors or ligands) involved in alternative or supplemental immunomodulatory pathways, such as CTLA4, TIM3, TIM4, OX40, CD40, GITR, 4-1-BB, CD27/CD70, ICOS, B7-H4, LIGHT, PD-1 or LAG3, in order to diminish further modulate the immunomodulatory effects. Furthermore, the multispecific antibody may bind to effecter molecules such as cytokines (e.g., IL-7, IL-15, IL-12, IL-4 TGF-beta, IL-10, IL-17, IFNg, Flt3, BLys) and chemokines (e.g., CCL21), which may be particularly relevant for down-modulating both acute and chronic immune responses.

In vitro methods are also suitable for preparing bi-specific and/or bivalent antibodies and antibody fragments. Digestion of antibodies to produce fragments thereof, particularly F(ab')2 fragments, can be accomplished using routine techniques known in the art. For instance, digestion can be performed using pepsin. Examples of pepsin digestion are described in International Patent Application WO2007035624 A1, which is hereby incorporated by reference. Pepsin digestion of antibodies cleaves the heavy chains near the hinge region. One or more of the disulfide bonds that join the heavy chains in the hinge region are preserved, so the Fab regions of the antibody remain joined together, yielding one F(ab')2 fragment. Pepsin completely digests the Fc fragment. The F(ab')2 fragment has two antigen binding sites and is still capable of cross-linking antigen. As the F(ab')2 fragment retains the specific binding character of the intact antibody, its utility is similar to the intact antibody. The Fc fragment typically acts as a marker signal for macrophages and the activation of lymphocytes for the recognition and phagocytosis of antigen-antibody complexes. F(ab')2 fragments, which lack the Fc fragment, are less likely to be recognized as foreign by a recipient receiving F(ab')2 antibody fragments.

A single chain variable fragment can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a linker have been developed without significantly disrupting antigen binding or specificity of the binding. The linker is chosen to permit the heavy chain and light chain to bind together in their proper conformational orientation. The linker is usually rich in glycine for flexibility, and typically also includes serine or threonine for solubility. The linker can link, for example, the N-terminus of the $V_H$ with the C-terminus of the $V_L$, or vice versa. scFv can also be created directly from subcloned heavy and light chains derived from a hybridoma. Preferably, the scFv retains, or improves or increases the specificity of the original immunoglobulin, while removing of the constant regions and introducing the linker.

Exemplary antigen binding molecules that include two or more single chain variable fragments (scFv) including the light chain variable region ($V_L$) of Herceptin and/or m590, or a variant thereof, and the heavy chain variable region ($V_H$) of Herceptin and/or m590, or a variant thereof of the antibody Herceptin and/or m590 include, but are not limited to, divalent-scFv (di-scFv), trivalent-scFv (tri-scFv), multivalent-scFv (multi-scFv), diabodies, triabodies, tetrabodies, etc., of scFvs.

Divalent single chain variable fragments can be engineered by linking two scFvs. This can be done by producing a single peptide chain with two $V_H$ and two $V_L$ regions, yielding a di-scFvs referred to as a tandem di-scFv. ScFvs can also be designed with linker peptides that are too short for the two variable regions to fold together (about five amino acids), forcing scFvs to dimerize and form a divalent single chain variable fragment referred to as a diabody. Diabodies have been shown to have dissociation constants up to 40-fold lower than corresponding scFvs, indicating that they have a much higher affinity to their target. Even shorter linkers (one or two amino acids) lead to the formation of trimers (triabodies or tribodies). Tetrabodies have also been produced and have been shown to exhibit an even higher affinity to their targets than diabodies.

The disclosed antigen binding molecules includes antigen binding antibody fragments and fusion proteins of Herceptin and/or m590 and variants thereof that typically bind to the same epitope as monoclonal antibody Herceptin and/or m590. In the most preferred embodiments, the antigen binding molecule is a di-, tri-, or multivalent scFv. Although the antigen binding antibody fragment or fusion protein of the antigen binding molecule can include additional antibody domains (e.g., constant domains, hinge domains, etc.), it preferably does not. Herceptin and/or m590 binds DNA and inhibits DNA repair, which is synthetically lethal to DNA repair-deficient cells. This function is independent of any Herceptin and/or m590 constant regions. By contrast, non-penetrating antibodies such as cetuximab that target extracellular receptors depend in part on Fc-mediated activation of ADCC and complement to exert an effect on tumors. Elimination of the Fc from non-penetrating antibodies could therefore diminish the magnitude of their effect on tumors, but Fc is not required for Herceptin and/or m590 to have an effect on cancer cells. Therefore, Herceptin and/or m590 fragments or fusions that lack an Fc region should be unable to activate ADCC and complement and therefore carry a lower risk of nonspecific side effects.

The disclosed antibody fragments and polypeptides can be linked together to form multi-specific and/or multivalent antibody fragments and polypeptides. For example, scFv and other forms of non-specific binding fragments can be linked together to form bi- and multi-specific binding fragments. The term "linker" as used herein includes, without limitation, peptide linkers. The peptide linker can be any size provided it does not interfere with the binding of the epitope by the variable regions. In some embodiments, the linker includes one or more glycine and/or serine amino acid residues. Monovalent single-chain antibody variable fragments (scFvs) in which the C-terminus of one variable domain are typically tethered to the N-terminus of the other variable domain via a 15 to 25 amino acid peptide or linker. The linker is chosen to permit the heavy chain and light chain to bind together in their proper conformational orientation. Linkers in diabodies, triabodies, etc., typically include a shorter linker than that of a monovalent scFv as discussed above. Di-, tri-, and other multivalent scFvs typically include three or more linkers. The linkers can be the same, or different, in length and/or amino acid composition. Therefore, the number of linkers, composition of the linker(s), and length of the linker(s) can be determined based on the desired valency of the scFv as is known in the art. Preferably the linker(s) allows for or drives formation of a di-, tri-, and other multivalent scFv.

For example, a linker can include 4-8 amino acids. In another embodiment, a linker includes 15-20 amino acids, preferably 18 amino acids.

The scFv can be composed of an antibody fragment or fusion protein including an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of Herceptin and/or m590, and which binds to the epitope of Herceptin and/or m590, is selectively lethal to or selectively increases the radiosensitivity and/or chemosensitivity of cells deficient in DNA repair, or a combination thereof. The scFv can be composed of an antibody fragment or fusion protein that includes a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the variable heavy chain and/or light chain of Herceptin and/or m590, and which binds to the epitope of Herceptin and/or m590, is selectively lethal to or selectively increases the radiosensitivity and/or chemosensitivity of cells deficient in DNA repair, or a combination thereof. The determination of percent identity of two amino acid sequences can be determined by BLAST protein comparison. In preferred embodiments, scFv includes one, two, three, four, five, or more preferably, all six of the CDRs of the above-described preferred variable domains and which binds to the epitope of Herceptin and/or m590, is selectively lethal to or selectively increases the radiosensitivity and/or chemosensitivity of cells deficient in DNA repair, or a combination thereof.

Predicted complementarity determining regions (CDRs) of the heavy chain variable sequence for Herceptin and/or m590 are known in the art, see, for example, Zack, et al., *Immunology and Cell Biology,* 72:513-520 (1994) and GenBank Accession number AAA65679.1. Predicted complementarity determining regions (CDRs) of the light chain variable sequence for Herceptin and/or m590 are known in the art, see, for example, GenBank: AAA65681.1—immunoglobulin light chain, partial [*Mus musculus*].

In some embodiments, antibody fragment or fusion protein is modified to alter its half-life. In some embodiments, it is desirable to increase the half-life of the antibody fragment or fusion protein so that it is present in the circulation or at the site of treatment for longer periods of time. For example, where the antibody fragments or fusion proteins are being used alone to treat cancer, e.g., cancer cells having impaired DNA repair, it may be desirable to maintain titers of the antibody fragment or fusion protein in the circulation or in the location to be treated for extended periods of time. In other embodiments, the half-life of the antibody fragment or fusion protein is decreased to reduce potential side effects. For example, where the antibody fragment or fusion protein is being used in conjunction with radiotherapy or chemotherapy, the antibody fragment or fusion protein is preferably present in the circulation at high doses during the treatment with radiation or antineoplastic drug but is otherwise quickly removed from the circulation. Antibody fragments, such as Herceptin and/or m590 scFv, are expected to have a shorter half-life than full size antibodies. Other methods of altering half-life are known and can be used in the described methods. For example, antibody fragments and fusion proteins can be engineered with Fc variants that extend half-life, e.g., using Xtend™ antibody half-life prolongation technology (Xencor, Monrovia, Calif.).

The disclosed antibodies, fragments, and polypeptides can be produced by any method known in the art useful for the production of polypeptides, e.g., in vitro synthesis, recombinant DNA production, and the like. Preferably, the antibodies are produced by recombinant DNA technology. The HER2 and/or IGF-IR antibodies can be produced using recombinant immunoglobulin expression technology. The recombinant production of immunoglobulin molecules, including humanized antibodies are described in U.S. Pat. No. 4,816,397 (Boss et al.), U.S. Pat. Nos. 6,331,415 and 4,816,567 (both to Cabilly et al.), U.K. patent GB 2,188,638 (Winter et al.), and U.K. patent GB 2,209,757. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992). Additional information concerning the generation, design and expression of recombinant antibodies can be found in Mayforth, Designing Antibodies, Academic Press, San Diego (1993).

An exemplary process for the production of the recombinant chimeric HER2 and/or IGF-IR antibodies can include the following: a) constructing, by conventional molecular biology methods, an expression vector that encodes and expresses an antibody heavy chain in which the CDRs and variable region of a murine anti-human HER2 and/or IGF-IR monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-human HER2 and/or IGF-IR monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized HER2 and/or IGF-IR antibodies can include the following: a) constructing, by conventional molecular biology methods, an expression vector that encodes and expresses an anti-human HER2 and/or IGF-IR heavy chain in which the CDRs and a minimal portion of the variable region framework that are required to retain donor antibody binding specificity are derived from a non-human immunoglobulin, such as a murine anti-human HER2 and/or IGF-IR monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as a murine anti-human HER2 and/or IGF-IR monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells may be co-transfected with such expression vectors, which may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both. The host cell used to express the recombinant HER2 and/or IGF-IR antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and may be selected so as to have the desired expression and regulatory characteristics in the selected host cell. Other cell lines that may be used include, but are not limited to, CHO-K1, NSO, and PER.C6 (Crucell, Leiden, Netherlands).

Any of the above-described antibodies can be used to generate anti-idiotype antibodies using techniques well known to those skilled in the art (see, e.g., Greenspan, N. S. et al. (1989) "*Idiotypes: Structure And Immunogenicity,*" FASEB J. 7:437-444; and Nisinoff, A. (1991) "*Idiotypes: Concepts And Applications,*" J. Immunol. 147(8):2429-2438).

The binding properties of any of the above antibodies can, if desired, be further improved by screening for variants that exhibit such desired characteristics. For example, such antibodies can be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman, U. et al. (1995) "*Phage Display Of Disulfide-Stabilized Fv Fragments,*" J. Immunol. Methods, 182:41-50, 1995; Ames, R. S. et al. (1995) "*Conversion Of Murine Fabs Isolated From A Combinatorial Phage Display Library To Full Length Immunoglobulins,*" J. Immunol. Methods, 184:177-186; Kettleborough, C. A. et al. (1994) "*Isolation Of Tumor Cell-Specific Single-Chain Fv From Immunized Mice Using Phage-Antibody Libraries And The R-Construction Of Whole Antibodies From These Antibody Fragments,*" Eur. J. Immunol., 24:952-958, 1994; Persic, L. et al. (1997) "*An Integrated Vector System For The Eukaryotic Expression Of Antibodies Or Their Fragments After Selection From Phage Display Libraries,*" Gene, 187:9-18; Burton, D. R. et al. (1994) "*Human Antibodies From Combinatorial Libraries,*" Adv. Immunol. 57:191-280; PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art (such as those disclosed in PCT Publication WO 92/22324; Mullinax, R. L. et al. (1992) "*Expression Of A Heterodimeric Fab Antibody Protein In One Cloning Step,*" BioTechniques, 12(6):864-869; and Sawai et al. (1995) "*Direct Production Of The Fab Fragment Derived From The Sperm Immobilizing Antibody Using Polymerase Chain Reaction And cDNA Expression Vectors,*" Am. J. Reprod. Immunol. 34:26-34; and Better, M. et al. (1988) "*Escherichia coli Secretion Of An Active Chimeric Antibody Fragment,*" Science 240:1041-1043). Examples of techniques which can be used to produce single-chain Fvs and antibodies include those described in U.S. Pat. Nos. 4,946,778 and 5,258,498; Huston, J. S. et al. (1991) "*Protein Engineering Of Single-Chain Fv Analogs And Fusion Proteins,*" Methods in Enzymology 203:46-88; Shu, L. et al., "*Secretion Of A Single-Gene-Encoded Immunoglobulin From Myeloma Cells,*" Proc. Natl. Acad. Sci. (USA) 90:7995-7999; and Skerra. A. et al. (1988) "*Assembly Of A Functional Immunoglobulin Fv Fragment In Escherichia coli,*" Science 240:1038-1040.

Phage display technology can be used to increase the affinity of an antibody for HER2 and/or IGF-IR. This technique would be useful in obtaining high affinity antibodies that could be used in the disclosed combinatorial methods. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al. (1992) "*Antibody Engineering By Codon-Based Mutagenesis In A Filamentous Phage Vector System,*" J. Immunol. 149:3903-3913). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al. (1998) "*Stepwise In Vitro Affinity Maturation Of Vitaxin, An Alphav Beta3-Specific Humanized Mab,*" Proc. Natl. Acad. Sci. (USA) 95(11):6037-6042; Yelton, D. E. et al. (1995) "*Affinity Maturation Of The BR96Anti-Carcinoma Antibody By Codon-Based Mutagenesis,*" J. Immunol. 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site,*" J. Mol. Biol. 263:551-567).

The use of random mutagenesis to identify improved CDRs is contemplated. Phage display technology can alternatively be used to increase (or decrease) CDR affinity. This technology, referred to as affinity maturation, employs mutagenesis or "CDR walking" and re-selection uses the target antigen or an antigenic fragment thereof to identify antibodies having CDRs that bind with higher (or lower) affinity to the antigen when compared with the initial or parental antibody (see, e.g., Glaser, S. M. et al. (1992) "*Antibody Engineering By Codon-Based Mutagenesis In A Filamentous Phage Vector System,*" J. Immunol. 149:3903-3913).

Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased (or decreased) avidity to the antigen (e.g., ELISA) (see, Wu, H. et al. (1998) "*Stepwise In Vitro Affinity Maturation Of Vitaxin, An Alphav Beta3-Specific Humanized Mab*," Proc. Natl. Acad. Sci. (USA) 95(11):6037-6042; Yelton, D. E. et al. (1995) "*Affinity Maturation Of The BR96 Anti-Carcinoma Antibody By Codon-Based Mutagenesis*," J. Immunol. 155:1994-2004). CDR walking which randomizes the light chain may be used possible (see, Schier et al. (1996) "*Isolation Of Picomolar Affinity Anti-C-Erbb-2 Single-Chain Fv By Molecular Evolution Of The Complementarity Determining Regions In The Center Of The Antibody Binding Site*," J. Mol. Biol. 263: 551-567).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "Affinity maturation of antibodies assisted by in silico modeling," Proc. Natl. Acad. Sci. (USA) 105(26): 9029-9034.

The production and use of "derivatives" of any of the above-described antibodies and their antigen-binding fragments is particularly contemplated.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, chimeric or humanized variants of any of antibodies 1.3, 4.5 or 7.8, as well as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma RIII*," Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha (1 . . . 6) Dextran Increases Its Affinity For Antigen*," J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region*," J. Immunol. 143(8): 2595-2601; Routledge, E. G. et al. (1995) "*The Effect Of Aglycosylation On The Immunogenicity Of A Humanized Therapeutic CD3 Monoclonal Antibody,*" Transplantation 60(8):847-53; Elliott, S. et al. (2003) "*Enhancement Of Therapeutic Protein In Vivo Activities Through Glycoengineering*," Nature Biotechnol. 21:414-21; Shields, R. L. et al. (2002) "*Lack Of Fucose On Human IgG N-Linked Oligosaccharide Improves Binding To Human Fcgamma RIII And Antibody-Dependent Cellular Toxicity.*," J. Biol. Chem. 277(30): 26733-26740).

In some embodiments, a humanized antibody is a derivative. Such a humanized antibody comprises amino acid residue substitutions, deletions or additions in one or more non-human CDRs. The humanized antibody derivative may have substantially the same binding, better binding, or worse binding when compared to a non-derivative humanized antibody. In specific embodiments, one, two, three, four, or five amino acid residues of the CDR have been substituted, deleted or added (i.e., mutated).

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

Derivatized antibodies may be used to alter the half-lives (e.g., serum half-lives) of parental antibodies in a mammal, preferably a human. Preferably such alteration will result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the humanized antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor. The humanized HER2 and/or IGF-IR antibodies can be engineered to increase biological half-lives (see, e.g. U.S. Pat. No. 6,277,375). For example, humanized HER2 and/or IGF-IR antibodies can be engineered in the Fc-hinge domain to have increased in vivo or serum half-lives.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The HER2 and/or IGF-IR antibodies may also be modified by the methods and coupling agents described by Davis et al. (See U.S. Pat. No. 4,179,337) in order to provide compositions that can be injected into the mammalian circulatory system with substantially no immunogenic response.

One embodiment encompasses modification of framework residues of the humanized HER2 and/or IGF-IR antibodies. Framework residues in the framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089; and Riechmann, L. et al. (1988) "Reshaping Human Antibodies For Therapy," Nature 332:323-327).

Yet another embodiment encompasses anti-human HER2 and/or IGF-IR antibodies (and more preferably, humanized antibodies) and antigen-binding fragments thereof that are recombinantly fused or chemically conjugated (including both covalently and non-covalently conjugations) to a heterologous molecule (i.e., an unrelated molecule). The fusion does not necessarily need to be direct, but may occur through linker sequences.

The disclosed polypeptides can also encompass fusion molecules and conjugates with other molecules that can enhance the inhibitory effect of the polypeptide. The generation of fusion molecules (e.g., proteins) and conjugates (e.g., through physical or chemical conjugation) is within the ordinary skill in the art and can involve the use of restriction enzyme or recombinant cloning techniques (see, e.g., U.S. Pat. No. 5,314,995, which is hereby incorporated by reference).

The fusion molecule (e.g., proteins and nucleic acid molecules) or conjugate can comprise one or more of SEQ ID NOs: 1-14 in combination with any suitable second molecule. For example, the fusion molecule or conjugate can comprise one or more of SEQ ID NOs: 1-11 in combination with a neutralizing scFv antibody fragment or a Fab fragment (e.g., that binds to an epitope of HER2 and/or IGF-IR).

Toxins are poisonous substances that usually are produced by plants, animals, or microorganisms that, in sufficient doses, are lethal. Preferred toxin for use in the fusion molecules or conjugates described herein include *Pseudomonas* toxin, Diphtheria toxin, tetanus toxoid, ricin, cholera toxin, Shiga-like toxin (SL T-I, SL T-II, SL T-10 IIV), L T toxin, C3 toxin, Shiga toxin, pertussis toxin, tetanus toxin, *Pseudomonas* exotoxin, alorin, saporin, modeccin, and gelanin. The polypeptide (e.g., antibody, or a binding fragment thereof), and the toxin can be linked in several ways. If the hybrid molecule is produced by expression of a fused gene, a peptide bond serves as the link between the toxin and the polypeptide.

Alternatively, the toxin and the polypeptide can be produced separately and later coupled (e.g., by means of a non-peptide covalent bond). For example, the covalent linkage may take the form of a disulfide bond. In this case, the nucleic acid molecule encoding the polypeptide can optionally contain an extra cysteine codon. The cysteine codon can be positioned so as not to interfere with the binding activity of the molecule. The toxin molecule can be derivatized with a sulfhydryl group reactive with the cysteine of the modified polypeptide. In the case of a peptide toxin, this optionally can be accomplished by inserting DNA encoding a cysteine codon into the nucleic acid molecule encoding the toxin. In another alternative, a sulfhydryl group, either by itself or as part of a cysteine residue, can be introduced into the disclosed polypeptide using solid phase polypeptide techniques.

Moreover, the polypeptides described herein can be combined with other well-known therapies already in use. The combination of the polypeptide described herein and one or more other therapeutic agents can provide a greater therapeutic effect than either agent alone, and preferably generate an additive or a synergistic effect with current treatments. For example, the disclosed polypeptide can be combined with other therapies targeting the IGF-IR, HER2 or other components in the IGF and HER2 signaling network, including IGF-I, IGF-II, IGF binding proteins, HER1/HER3/HER4 binding proteins, such as anti-HER2 monoclonal antibody Herceptin, anti-HER1 monoclonal antibody (Roche), anti-HER3 monoclonal antibody (Genentech), anti-IGF-IR monoclonal antibodies CP751,871 (Pfizer), Neuregulin/Heregulin (Sigma), Heparin-binding EFG-like growth factor (Sigma), betacellulin (Peprotech), MK-0646

(Pierre-Fabre/Merck), AmG479 (Amgen), IMC-A12 (ImClone), R1507 (Hoffmann LaRoche), robatumumab (Schering-Plough), and cytokine immune enhancement therapy (interleukin (IL)-2, IL-12, CD40L+IL-12, IL-7, and interferons (IFNs)). Such therapies can be administered in the manner already in use for the known treatment providing a therapeutic effect.

The disclosed polypeptide can be a neutralizing antibody against HER2 and IGF-IR useful for cancer therapy. In some embodiments, the disclosed antibody (or binding fragment thereof) can inhibit HER2 and IGF-IR functions and can inhibit HER2- and IGF-IR-mediated signaling. The disclosed antibody (or binding fragment thereof) can have a high affinity for HER2 and IGF-IR and is specific for HER2 and IGF-IR.

In some embodiments, the antibody, or binding fragment thereof, physically associates with other molecules (e.g., anti-IGF-IR antibodies, anti-HER1/2/3 antibodies) to inhibit HER2- and IGF-IR-mediated signaling. In other words, the polypeptide specifically binds, specifically reacts with, or specifically interacts with other target molecules (e.g. IGF-I, -II, IGF binding proteins, HER1/3/4 binding proteins). In some alternative embodiments, the polypeptide does not substantially physically associate with other molecules.

The epitopes recognized by the polypeptides described herein can be used as cancer vaccine immunogens, as active portions of cancer vaccine immunogens, and as targets for inhibitors of HER2 and IGF-IR signaling networks. For example, the epitopes described herein (or polypeptides comprising the epitopes) can be used as targets to isolate antibodies that, other than those described herein, bind to the epitopes described herein. These antibodies can be used in the treatment and diagnosis of cancer.

While it is possible to administer (for example, as a vaccine) an epitope (or polypeptide comprising the epitope) that is recognized by the disclosed antibodies in a pure or substantially pure form, the epitope can be formulated into a pharmaceutical composition, formulation, or preparation. Accordingly, the disclosure encompasses a composition containing an epitope (or polypeptide comprising the epitope) recognized by the antibody described herein. The composition can further contain one or more pharmaceutically acceptable carriers (as described herein) and, optionally, other therapeutic ingredients. The composition comprising such epitope can be used therapeutically or to otherwise generate an immune response.

For example, a vaccine is provided to enhance the patient's own immune response to the antigens present due to tumorigenesis. Such vaccine, which acts as an immunogen, optionally can be a partially or substantially purified recombinant polypeptide containing the epitope or an analog thereof. The polypeptide comprising the epitope can be conjugated with one or more lipoproteins, administered in liposomal form, or with an adjuvant. Also encompassed by the disclosure are methods of developing vaccines or immunogenic compositions using the epitopes described herein.

The disclosure is also directed to methods of downregulating HER2 and IGF-IR and inhibiting HER2- and IGF-IR-mediated signaling in a mammal. The methods involve administering an effective amount of the polypeptide (e.g. the antibody or a binding fragment thereof that specifically binds to human HER2 and IGF-IR), nucleic acid molecule that encodes the polypeptide, a vector comprising the nucleic molecule, a cell comprising the nucleic acid molecule and/or vector, or compositions comprising the foregoing, to the mammal, wherein cancer cell growth and cancer metastasis are reduced or inhibited. In some embodiments, the mammal is a human.

In some embodiments, a polypeptide (e.g. the antibody or a binding fragment thereof that specifically binds to human HER2 and IGF-IR), a nucleic acid molecule, a vector containing the nucleic acid encoding the polypeptide, or a cell (e.g., a host cell) containing any of the above can be administered to a mammal.

Also disclosed is a method for treating tumor or cancer, comprising administering to a subject in need of such treatment an effective amount of an isolated antibody, or a binding fragment thereof, to a subject. In some embodiments, disclosed nucleic acid molecules, vectors, and/or host cells can be administered for tumor or cancer therapy. In some embodiments, the disclosed compounds, compositions, and methods can be used to treat or ameliorate breast cancer, ovarian cancer, uterine cancer, prostate cancer, testicular germ cell tumor, glioblastoma multiforme, gastric cancer, esophagus cancer, lung cancer, liver cancer, and colon cancer.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "subject," as used herein, describes an organism, including mammals such as primates, to which treatment with the disclosed compositions can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

Vectors include, for example, nucleic acid vectors, such as naked DNA and plasmids, and viral vectors, such as retroviral vectors, parvovirus-based vectors (e.g., adenoviral-based vectors and adeno-associated virus (AAV)-based vectors), lentiviral vectors (e.g., Herpes simplex (HSV)-based vectors), and hybrid or chimeric viral vectors, such as an adenoviral backbone with lentiviral components (see, e.g., Zheng et al., Nat. Biotech., 18(2), 176-80 (2000); International Patent Application WO 98/22143; International Patent Application WO 98/46778; and International Patent Application WO 00/17376) and an adenoviral backbone with AAV components (see, e.g., Fisher et al., Hum. Gene Ther., 7, 2079-2087 (1996)), all of which are hereby incorporated by reference). Vectors and vector construction are known in the art (see, e.g., Sambrook et al., Molecular Cloning: A Laboratory Manual, 2d edition, Cold Spring Harbor Laboratory, NY (1989); and Ausubel et al., Current Protocols in Molecular Biology, Green Publishing Associates and John Wiley & Sons, New York, N.Y. (1994), both of which are hereby incorporated by reference).

The vector can contain any suitable promoter and other regulatory sequences (e.g., transcription and translation initiation and termination codons, which are specific to the type of host) to control the expression of the nucleic acid sequence encoding the polypeptide. The promoter can be a native or normative promoter operably linked to the nucleic acid molecule described above. The selection of promoters, including various constitutive and regulated promoters, is within the skill of an ordinary artisan.

Examples of regulated promoters include inducible, repressible, and tissue-specific promoters. Specific examples include tetracycline-regulated promoters, steroid-regulated promoters, theophylline riboswitch, viral promoters, such as adenoviral promoters, cytomegalovirus promoters and AAV promoters. Additionally, combining the nucleic acid described above with a promoter is within the skill in the art.

Cells (e.g., isolated host cells) containing the above-described polypeptide or nucleic acid molecule encoding the polypeptide, optionally in the form of a vector, are also provided by the disclosure. Any suitable cell can be used. Examples include host cells, such as E. coli (e.g., E. coli Tb-1, TG-2, DHSa, XL-Blue MRF' (Stratagene), SA2821, and Y1090), Bacillus subtilis, Salmonella typhimurium, Serratia marcescens, Pseudomonas (e.g., P. aerugenosa), N. grassa, insect cells (e.g., Sf9, Ea4), yeast (S. cerevisiae) cells, and cells derived from a mammal, including human cell lines. Specific examples of suitable eukaryotic host cells include SKOV-3, SKBR3, MDA453, MCF-7, VERO, HeLa, 3T3, Chinese hamster ovary (CHO) cells, W138 BHK, COS-7, and MDCK cells. Alternatively, cells from a mammal, such as a human, to be treated in accordance with the methods described herein can be used as host cells.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., Molecular Biology: A Laboratory Manual, Cold Spring Harbor Laboratory, NY (1989); Davis et al., Basic Methods in Molecular Biology (1986); and Neumann et al., EMBO J. 1, 841 (1982), all of which are hereby incorporated by reference). In some embodiments, the cell containing the vector or nucleic acid molecule is transcribed and translated efficiently by the cell.

The disclosed antibodies can be administered parenteral by injection or by gradual infusion over time. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, antibodies, and derivatives thereof can be administered intravenously, intraperitoneally, intramuscularly, subcutaneously, intracavity, transdermally, topically, intraocularly, orally, intranasally, and can be delivered by peristaltic means.

The therapeutic compositions containing a disclosed antibody are conventionally administered intravenously, as by injection of a unit dose, for example. The term "unit dose" when used in reference to a disclosed therapeutic composition refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the patient to be treated, capacity of the patient's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration also are variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The nucleic acid molecules, vectors, cells, and polypeptides can be administered to a mammal alone, or in combination with a pharmaceutically acceptable carrier. By pharmaceutically acceptable is meant a material that is not biologically or otherwise undesirable (e.g., the material can be administered to a mammal, along with the nucleic acid, vector, cell, or polypeptide, without causing undesirable biological effects or interacting in a deleterious manner with other components of the pharmaceutical composition in which it is contained). The carrier is selected to minimize the degradation of the agent and to minimize adverse side effects in the mammal. The selection of carrier is well-known to one of ordinary skill in the art.

Suitable carriers and their formulations are described in Remington: The Science and Practice of Pharmacy (19th ed.) ed. A. R. Gennaro, Mack Publishing Company, Easton, Pa. (1995). Examples of pharmaceutical carriers include sterile water, saline, Ringer's solution, dextrose solution, and buffered solutions at physiological pH.

Typically, an appropriate amount of a pharmaceutically acceptable salt is used in the formulation to render the formulation isotonic. In some embodiments, the pH of the solution is from about 5 to about 8 (e.g., about 5.5, about 6, about 6.5, about 7, about 7.5, and ranges including any of these amounts therebetween), although pHs outside this range can be employed. In some embodiments, the pH is about 7 to about 7.5.

The disclosed pharmaceutical compositions can also include sustained-release preparations, such as semipermeable matrices of solid hydrophobic polymers containing the polypeptide, which matrices are in the form of shaped articles (e.g., films, liposomes, or microparticles). It will be apparent to those persons skilled in the art that certain carriers may be more preferable depending upon, for instance, the route of administration and the concentration of composition being administered.

Examples of compositions (e.g., pharmaceutical compositions) containing the nucleic acid molecule, vector, cell, or polypeptide can include carriers, thickeners, diluents, buffers, preservatives, surface active agents and the like. The compositions can also include one or more active ingredients, such as anti-IGF-I, -II antibodies, chemotherapy drugs, and the like. The compositions described herein can be approved for use by the U.S. FDA or the equivalent in other countries. The composition (e.g., pharmaceutical composition) containing the nucleic acid molecule, vector, cell, or polypeptide can be administered in any suitable manner depending on whether local or systemic treatment is desired, and on the area to be treated.

If the composition is to be administered parenterally, the administration is generally by injection. Injectables can be prepared in conventional forms, either as liquid solutions or suspensions, solid forms suitable for being prepared as a solution or suspension prior to injection, or as emulsions. Additionally, parental administration can involve the preparation of a slow-release or sustained-release system, such that a constant dosage is maintained (see, e.g., U.S. Pat. No. 3,610,795, which is hereby incorporated by reference). Preparations for parenteral administration include sterile aqueous or nonaqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases and the like.

The compositions can be in a form of acid- or base-addition salts, obtainable by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The nucleic acid molecules, vectors, or polypeptides can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

The exact amount of the compositions required to treat cancer may vary, depending on the species, age, gender, weight, and general conditions of the mammal, the particular polypeptide, nucleic acid, vector, or cell used, the route of administration, and whether other drugs are included in the regimen. Thus, it is not possible to specify an exact amount for every composition. However, an appropriate, suitable amount can be determined by one of ordinary skill in the art using only routine experimentation given the teachings herein. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days (or any suitable period of time to advance treatment). The composition can be administered immediately upon determination of cancer and continuously or intermittently administered.

The term "effective amount," as used herein, refers to an amount that is capable of treating or ameliorating a disease or condition or otherwise capable of producing an intended therapeutic effect. In some embodiments, an effective amount is an amount that is useful for treating or ameliorating tumor or cancer. In some embodiments, an effective amount enables an inhibition or reduction of cancer cell growth or metastasis in a subject. Effective dosages and schedules for administering the therapeutic agents and compositions described herein can be determined empirically, and making such determinations is routine to one of ordinary skill in the art.

The skilled artisan will understand that the dosage of the polypeptides varies, depending upon, for example, the route of administration, the particular polypeptide to be used, other drugs being administered, and the age, condition, gender and seriousness of the disease in the subject as described above. An effective dose of the polypeptide described herein generally ranges between about 1 ng/kg of body weight and 100 mg/kg of body weight. Examples of such dosage ranges are, e.g., about 1 µg-100 µg/kg, about 100 µg-1 mg/kg, about 1 mg/kg-10 mg/kg, or about 10 mg-100 mg/kg, once a month, a week, bi-weekly, daily, or two to four times daily.

Guidance in selecting appropriate doses for anti-HER2/anti-IGF-IR antibodies, such as the polypeptides described herein, is found in the literature on therapeutic uses of antibodies (see, e.g., Handbook of Monoclonal Antibodies, Ferrone et al., eds., Noges Publications, Park Ridge, N.J., (1985); and Smith et al., Antibodies in Human Diagnosis and Therapy, Haber et al., eds., Raven Press, New York (1977), all of which are hereby incorporated by reference. A typical daily dosage of the polypeptide used might range from about 1 µg/kg to up to about 100 mg/kg of body weight or more per day, depending on the factors mentioned above. For example, the range can be from about 100 mg to about 1 g per dose. Nucleic acids, vectors, and host cells should be administered so as to result in comparable levels of production of polypeptides.

The disclosure also includes kits comprising the polypeptides, nucleic acid molecules, vectors, cells, epitopes, or compositions of the foregoing. The kits can include a separate container containing a suitable carrier, diluent, or excipient. The kits also can include an adjuvant, cytokine, antiviral agent, immunoassay reagents, PCR reagents, radiolabels, and the like. Additionally, the kits can include instructions for mixing or combining ingredients and/or administration.

The disclosure also provides a method of detecting HER2 and IGF-IR in a mammal comprising contacting a sample obtained from the mammal with the polypeptide described herein. If the antigens are present in the mammal, to which the polypeptide can bind, a complex forms between the polypeptide and the antigens. Detection of the complex indicates the presence of elevated HER2 and IGF-IR in the mammal.

The sample from the mammal can be of any suitable sample to detect the presence of HER2 and IGF-IR. The complex can be detected by any suitable manner. The polypeptides described herein are utilizable as labeled molecules employed in radioimmunoassay (RIA) or enzyme immunoassay (EIA), particularly enzyme linked immunosorbent assay (ELISA), by introducing thereto radioactive substances such as 1125, 1131, H3 (tritium), C14, and the like; various enzyme reagents such as peroxidase (PDX), chymotrypsinogen, procarboxypeptidase, glyceraldehyde-3-phosphate dehydrogenase, amylase, phosphorylase, DNase, P-Nase, i3-galactosidase, glucose-6-phosphate dehydrogenase, ornithine decarboxylase, and the like. The radioactive substance can be introduced in a conventional manner. For example, the introduction of radioactive iodine, 1125, can be carried out by the oxidative ionization method using chloramine T (see, e.g., Hunter et al., Nature, 194, 495-496 (1962)) or by using the Bolten-Hunter reagent (1125-iodinated p-hydroxyphenyl propionic acid N-hydroxy-succinimide ester), which is hereby incorporated by reference.

The label for use in the method can be any suitable label known in the art, such as biotinylated proteins or peptides.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Materials and Methods

DNA Preparation

The gene encoding the extracellular domain (ectodomain) of IGF-IR was amplified from the pBlueScript-IGF-IR construct P08069 (Zhang et al., MAbs. 1:475-80 (2009)), and subcloned into the pSecTag2C vector at the EcoR I and Not I sites. The gene encoding HER2 ectodomain was amplified from SKOV-3 cell by reverse transcriptase PCR, and subsequently cloned into the pSecTag2A vector at the Xho I and Sfi I sites. Both constructs were confirmed by DNA sequencing.

Recombinant ectodomains of IGF-IR and HER2 were produced by transient transfection of 293T cells. Expression in transfectants was enhanced by the transduction of vaccinia virus vTF7-3 encoding bacteriophage T7 RNA polymerase. 72 h post transfection, culture supernatants were collected and His-tagged ectodomains purified by immobilized metal-affinity chromatography.

Cell Lines, Antibodies and Chemicals

Breast cancer MCF-7 cells were cultured in DMEM medium (Invitrogen) supplemented with 10% heat-inactivated FBS and 1% penicillin/streptomycin (P/S). Ovarian cancer SKOV-3 cells were cultured in McCoy's 5A medium (Hyclone) supplemented with 10% heat-inactivated FBS and 1% P/S. The following primary mAbs were purchased from Cell Signal Technology: rabbit anti-Phospho-AKT (Thr308) (C31E5E), rabbit anti-Phospho-p44/42 MAPK (ERK1/2) (Thr202/Tyr204) (D13.14.4E) XP, rabbit anti-Akt (pan) (11E7), rabbit anti-P44/42 MAPK (ERK1/2) (137F5), and rabbit anti-GAPDH mAb (14C10). The secondary antibodies were purchased from Jackson ImmunoResearch. Xenolight D-luciferin was purchased from Caliper Life Sciences.

Expression and Purification of Herceptin and m590, and Bi-Ab

Herceptin and m590 were expressed by transient transfection of 293F cells (Invitrogen) with recombinant plasmids pDR12-Herceptin and pDR12-m590, respectively. Bi-Ab was expressed by transiently co-transfecting 293F cells with pDR12-Herceptin-366 and pDR12-m590-407 plasmids. Recombinant antibodies were purified from the culture supernatants by Protein A (GE Healthcare) affinity purification.

Indirect ELISA

Recombinant ectodomains of IGF-IR or HER2 (2 mg/ml in both cases) were coated on 96-well high-binding ELISA plates at 4° C. overnight. The plates were washed and blocked with 3% BSA in PBS at 37° C. for 2 h. Two-fold serially diluted mAb Herceptin or m590 were added to the wells and the bound mAbs were detected by HRP conjugated anti-human Fc as secondary antibody and TMB substrate. Optical density at 450 nm (OD450 nm) was measured after color development at RT for 30 min. In the case of Bi-Ab, recombinant IGF-IR ectodomains were coated on the plates. Following addition of 2-fold serially diluted Bi-Ab and incubation at RT for 2 h, plates were washed and biotinylated HER2 ectodomain (2 μg/ml) was added to each well. Bound HER2 ectodomains were detected by HRP conjugated streptavidin and TMB substrate.

Western Blotting

MCF-7 or SKOV-3 cells in complete medium were seeded in 6-well plates. When cells reached 70-80% confluence, they were incubated in serum-free medium overnight. Cells were treated with antibodies for 30 min, followed by addition of 1.5 nM IGF-I and further incubation for 30 min. Cells were then lysed and 10 μl of cell lysates from each sample was resolved by 12% SDS-PAGE. Once the proteins were transferred, PVDF membranes were blocked with 5% skim milk in PBS for 30 min, incubated with primary antibodies, and then secondary antibodies. The membranes were extensively washed after each incubation step. The Western blot signal was detected by Western Bright ECL-HRP substrate (Advansta).

Flow Cytometry

MCF-7 or SKOV-3 cells were detached using enzyme-free cell-disassociation buffer (Invitrogen), washed twice with PBS, and incubated at 4° C. for 2 h with antibodies in fluorescence-activated cell sorting (FACS) buffer (1% FBS in PBS). Cell surface bound antibodies were detected using PE conjugated to anti-human Fc by incubation at 4° C. for 1 h followed by washing twice with FACS buffer and fixation with 2% paraformaldehyde in FACS buffer. The stained cells were analyzed with a BD flow cytometer and FlowJo software.

ADCC Assay

The flow cytometry-based ADCC assay has been described previously (Srivastava et al., J. Virol. 87:5831-40 (2013)). Here, we used SKOV-3 cells as target cells and healthy human volunteers PBMCs as effector cells at an E/T ratio of 25/1. Briefly, SKOV-3 cells were stained with PKH-67, then mixed with antibodies and PBMCs. Following 2 h of incubation, 7-AAD was added to the mixture. Following several washes, the samples were analyzed by FACS AriaIII flow cytometer using BD FACS Diva software. Percent cell death was determined by software analysis of four identifiable cell populations, live effector cells (no dye), dead effector cells (7-AAD positive), live target cells (PKH-67 positive) and dead target cells (PKH-67 and 7-AAD double positive). Percent ADCC was calculated as [(% experimental lysis−% spontaneous lysis)/(% maximum lysis−% spontaneous lysis)]×100, in which "% spontaneous lysis" referred to percent dead target cells mixed with effectors in the absence of antibodies, and "% maximum lysis" referred to percent dead target cells mixed with effectors in the presence of 1% TRITON™ X-100. "% experimental lysis" referred to percent dead target cells mixed with effectors in the presence of antibodies. The assay was performed in duplicate and repeated once. One representative set of data was shown in this report.

Cell Proliferation Assay

Antibodies were serially diluted in culture medium containing 2% FBS and mixed with equal volume of SKOV-3 cells containing 3 nM IGF-I. Cell/Ab mixtures were then plated onto 96-well cell culture plates with a final concentration of 2,000 cells per well and 1.5 nM IGF-I. The plates were incubated at 37° C. with 5% CO2 for 72 h, and cell proliferation levels were detected by Cell Titer 96 Aqueous Non-Radioactive Cell Proliferation Assay Kit (Promega).

Construction of "Knobs-into-Holes" CH3 Variants

The humanized Herceptin heavy chain (HC) and light chain (LC) genes [DrugBank: Trastuzumab (DB00072) (BIOD00098, BTD00098)] and HC and LC genes from m590 were synthesized and cloned into the mammalian expression plasmid pDR12 obtained from Dr. Dennis Burton, Scripps Research Institute, California, (see, U.S. Pat. No. 5,804,440), which contains the human IgG1 heavy chain genomic DNA constant region. Two mutations were introduced in the CH3 domains of pDR12-Herceptin (T366Y) and pDR12-m590 (Y407T) using a site-directed mutagenesis kit (Stratagene). The primers for the mutagenesis were: T366Y-F: 5'-CCAGGTCAGCCTGTACTGCCTGGT-CAAAG-3', (SEQ ID NO: 17) and T366Y-R: 5'-CTTTGAC-CAGGCAGTACAGGCTGACCTGG-3'; (SEQ ID NO: 18) and Y407T-F: 5'-CTCCTTCTTCCTCACCAGCAAGCT-CACCG-3', (SEQ ID NO: 19) and Y407T-R: 5'-CGGT-GAGCTTGCTGGTGAGGAAGAAGGAG-3' (SEQ ID NO: 20). Mutations were confirmed by DNA sequencing. The resultant plasmids were designated as pDR12-Herceptin-366 and pDR12-m590-407, respectively. pDR12-m590-366 and pDR12-Herceptin-407 can also be created and used for production of anti-HER2/IGF-IR bi-specific antibodies.

Generation of the Luciferase-Expressing SKOV-3 Stable Cell Line 293T cells were transiently co-transfected with recombinant plasmid encoding HIV-1 Gag and Polymerase genes (Gag-pol), Luc-expressing plasmid, and VSV backbone plasmid at a ratio of 2/2/1 (Gag-pol/Luc/VSV). After transfections (36-48 h), culture supernatants containing Luc-lentivirus was collected, and then equally mixed with fresh culture medium followed by addition of polybrene to a final concentration of 8 mg/ml. Nine milliliters of the mixture were added to SKOV-3 cells seeded in 100-mm dishes and incubated at 37° C. for 6 h in 5% CO2. Three milliliters of culture medium containing 8 mg/ml polybrene were then added to the dish. Following overnight incubation, infection medium was removed and cells cultured in fresh McCoy's 5A medium containing 1 mg/ml puromycin. After 3-5 passages, limiting dilution was performed and single cell clones were screened by luciferase assay. The single cell clone expressing the highest level of luciferase was expanded and titrated by imaging in a 96-well plate.

Establishment of a Tumor Xenograft Mouse Model and the Mouse Study

This study was approved by HKU Committee on Using Live Animals in Teaching and Research (CULATR #2514-11). Nude BALB/c female mice, 4-6-weeks-old, were obtained from the Animal Centre of the University of Hong Kong. To establish a cancer xenograft mouse model, a pilot experiment was carried out by subcutaneously injecting different numbers of SKOV3-Luc cells into nude mice and analyzing by imaging at different time points. The optimal cell numbers that yielded sustainable and increasing luminescence intensity in the regions of interest (ROI) were determined. The mouse study was carried out as follow: on day 0, SKOV-3-Luc cells were resuspended in plain McCoy's 5A medium and 3 million of the cells were injected subcutaneously into each nude mouse. On day 1, KETAMINE/XYCAZINE/PBS at a ratio of 1/1.2/7.8 were mixed and 40 µl (2.5 µl/g body weight) of the anesthetic mixture was injected subcutaneously into each mouse. D-luciferin (100 µl) at a concentration of 30 mg/ml in DPBS (5 µl/g body weight) was then injected intra-peritoneally (i.p.) into each mouse (each mouse received 300 mg luciferin/kg body weight). About 15 min post injection, mice were imaged for luminescence intensity in the regions of interest (ROI) using Xenogen IVIS 100 in vivo imaging system. Mice were then randomized, so that each group of mice had approximately the same average luminescence intensity. Each group had 7 mice and a total of 4 groups were formed corresponding to Herceptin, m590, Bi-Ab, and Comb treatment conditions. Each antibody (100 mg) or antibody combination (100 mg total) were injected by i.p. into each mouse on days 1, 4, 6 and 8. Mouse imaging was repeated on days 4, 6, 8, 11, 15, 25, and 35.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Simultaneous Binding of HER2 and IGF-IR by Anti-HER2/Anti-IGF-IR Antibodies

This Example used the "knobs-into-holes" approach to generate an anti-IGF-IR/anti-HER2 hybrid IgG. A "knob" mutant was created by replacing a Threonine with Tyrosine (T366Y) in the CH3 domain of Herceptin. A "hole" mutant was made by replacing a Tyrosine with Threonine (Y407T) in the CH3 domain of m590. Co-transfection of 293F cells with the "knob" and "hole" plasmids resulted in the production of stable heterodimers that exhibited bi-specificity for both HER2 and IGF-IR (FIG. 1).

Bi-specific anti-HER2/anti-IGF-IR antibodies can simultaneously bind recombinant IGF-IR (coated) and HER2 ectodomains by indirect ELISA.

The bi-specific antibody (Bi-Ab) bound to recombinant IGF-IR and HER2 ectodomains (FIG. 1B) and to overexpressed, membrane-associated IGF-IR and HER2 on SKOV-3 cells (FIG. 1C). Compared to breast cancer MCF-7 cells used in our previous study, cancer SKOV-3 cells express both high levels of HER2 and IGF-IR (FIG. 1A). Similar to the two original antibodies, m590 and Herceptin, Bi-Ab bound to SKOV-3 in a dose-dependent manner (FIG. 1D). Moreover, flow cytometry analysis revealed that Herceptin and Bi-Ab have a similar binding profile which shows two peaks in the histogram (FIG. 1C), suggesting that cell surface HER2 proteins may have multiple conformational or organizational states.

FIG. 1B shows anti-HER2/anti-IGF-IR antibodies bound to recombinant IGF-IR ectodomains coated on 96-well high-binding ELISA plates. Following addition of the anti-HER2/anti-IGF-IR antibodies to recombinant IGF-IR-coated plates biotinylated recombinant HER2 ectodomains were added. Bound HER2 ectodomains were detected by HRP conjugated streptavidin and TMB substrate.

Example 2

Bi-Ab Inhibits Receptor Phosphorylation and Down-Regulates Downstream PI3K/Akt and MAPK Signaling The present inventor has reported that m590 blocks ligand-induced IGF-IR phosphorylation in breast cancer MCF-7 cells (Zhang et al., MAbs. 1:475-80 (2009)), and inhibits MCF-7 cell proliferation and migration (Fu et al., Chinese Journal of Experimental Surgery 29:824-6 (2012)).

Figure 2:
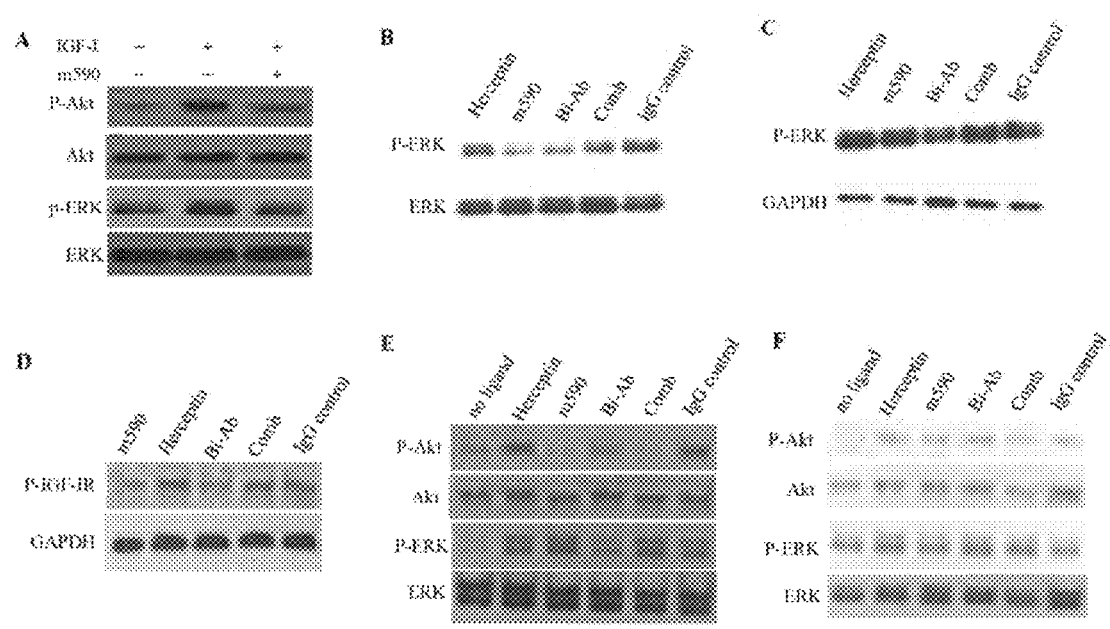
FIG. 2 shows inhibition of breast cancer cell signaling by anti-HER2/anti-IGF-IR in comparison with m590 and Herceptin alone or in combination. (A) Inhibition of IGF-I (1.5 nM) induced phosphorylation of Akt and ERK by m590 (40 nM) in MCF-7 cells. (B-C) Inhibition of ERK phosphorylation by the antibodies in MCF-7 (B) and SKOV-3 (C) cells in the absence of IGF-I. (D) Inhibition of IGF-I (1.5 nM) induced phosphorylation of IGF-IR in SKOV-3 cells. (E-F) Inhibition of IGF-I (1.5 nM) induced phosphorylation of Akt and ERK in MCF-7 (E) and SKOV-3 (F) cells. All antibodies were tested at 100 µg/ml (B-F).

This Example shows that m590 inhibited ligand-induced phosphorylation of Akt and ERK in MCF-7 cells (FIG. 2A). In addition, this Example compared the effects of Bi-Ab, m590 and Herceptin on phosphorylation of ERK in MCF-7 (FIG. 2B) and SKOV-3 cells (FIG. 2C) in the absence of ligand.

In MCF-7 cells, both m590 and Bi-Ab inhibited ERK phosphorylation, and Comb treatment slightly reduced ERK phosphorylation (FIG. 2B); but in SKOV-3 cells, only Bi-Ab weakly inhibited ERK phosphorylation (FIG. 2C).

Herceptin did not have inhibitory effect on ERK phosphorylation in both cell lines (FIGS. 2B and 2C). We then compared the effects of Bi-Ab, m590 and Herceptin on phosphorylation of IGF-IR in SKOV-3 cells (FIG. 2D) and downstream signaling in MCF-7 (FIG. 2E) and SKOV-3 cells (FIG. 2F) in the presence of ligand (IGF-I).

Both m590 and Bi-Ab inhibited phosphorylation of IGF-IR in SKOV-3 cells compared to non-specific human IgG control. Treatment with Herceptin or Comb did not result in decreased levels of phosphorylated IGF-IR in SKOV-3 cells (FIG. 2D).

In MCF-7 cells, m590 and Bi-Ab, as well as Comb inhibited ligand-induced phosphorylation of Akt, but only Bi-Ab inhibited ligand-induced phosphorylation of ERK (FIG. 2E). Treatment with Herceptin slightly enhanced ligand-induced phosphorylation of Akt in MCF-7 cells (FIG. 2E, lane 2).

None of the antibodies showed inhibitory effects on ligand-induced phosphorylation of Akt and ERK in SKOV3 cells at the antibody concentration (100 µg/ml) tested (FIG. 2F).

These results indicate that co-expression of both high levels of HER2 and IGF-IR in cancer cells raises the bar for antibodies to interfere with the receptor phosphorylation and downstream signaling, especially when the ligand (IGF-I) is present. Herceptin was ineffective in inhibiting phosphorylation of Akt and ERK in both MCF-7 and SKOV-3 cells in the presence or absence of IGF-I. Bi-Ab and m590 were equally effective in inhibiting phosphorylation of Akt and ERK in MCF-7 cells in the absence of ligand and in inhibiting ligand-induced Akt phosphorylation in MCF-7 cells, but Bi-Ab was more effective than m590 in inhibiting ERK phosphorylation in SKOV-3 cells in the absence of ligand, and in inhibiting ligand-induced ERK phosphorylation in MCF-7 cells.

Example 3

Bi-Ab More Effectively Inhibits Cancer Cell Proliferation than Herceptin and M590 In Vitro, and Contains ADCC Activity The results show that Bi-Ab attenuates the PI3K/Akt and MAPK pathways; this prompted us to analyze the effects of Bi-Ab on cancer cell proliferation.

Figure 3:
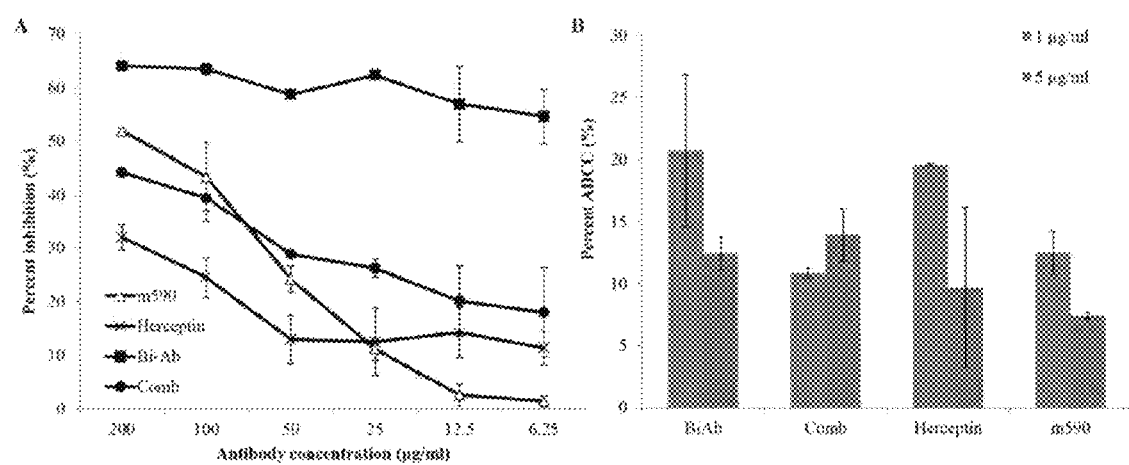
FIG. 3 shows inhibition of ovarian cancer SKOV-3 cell proliferation by anti-HER2/anti-IGF-IR and its ADCC activity in comparison with Herceptin and m590 alone or in combination (Comb). (A) Inhibition of SKOV-3 cell proliferation in MTT assay. (B) Percent ADCC of the antibodies at 1 and 5 µg/ml of antibody concentration. Each antibody dilution was tested in triplicate in both assays, and each assay was repeated once and one set of data was shown.

Bi-Ab treatment effectively inhibited SKOV-3 cell proliferation in vitro (FIG. 3A). Notably, although Comb treatment showed enhanced inhibition of SKOV-3 proliferation compared with Herceptin treatment alone, both treatment conditions were less potent than Bi-Ab (FIG. 3A). Moreover, m590 inhibited SKOV-3 cell proliferation, but its effect decreased sharply as m590 concentration decreased (FIG. 3A).

To investigate whether "knob" and "hole" mutations affected Fc-mediated effector function, we tested Bi-Ab for ADCC activity in a flow-cytometry based assay using SKOV-3 as target cells and healthy human peripheral blood mononuclear cells (PBMCs) as effector cells. The assay revealed that Bi-Ab has ADCC activity comparable to or slightly higher than that of m590, Herceptin, and the combination of m590 and Herceptin (Comb) (FIG. 3B). These results suggest Bi-Ab remains effective in killing HER2- and/or IGF-IR-expressing tumor cells through ADCC in vivo.

Example 4

Figure 4:
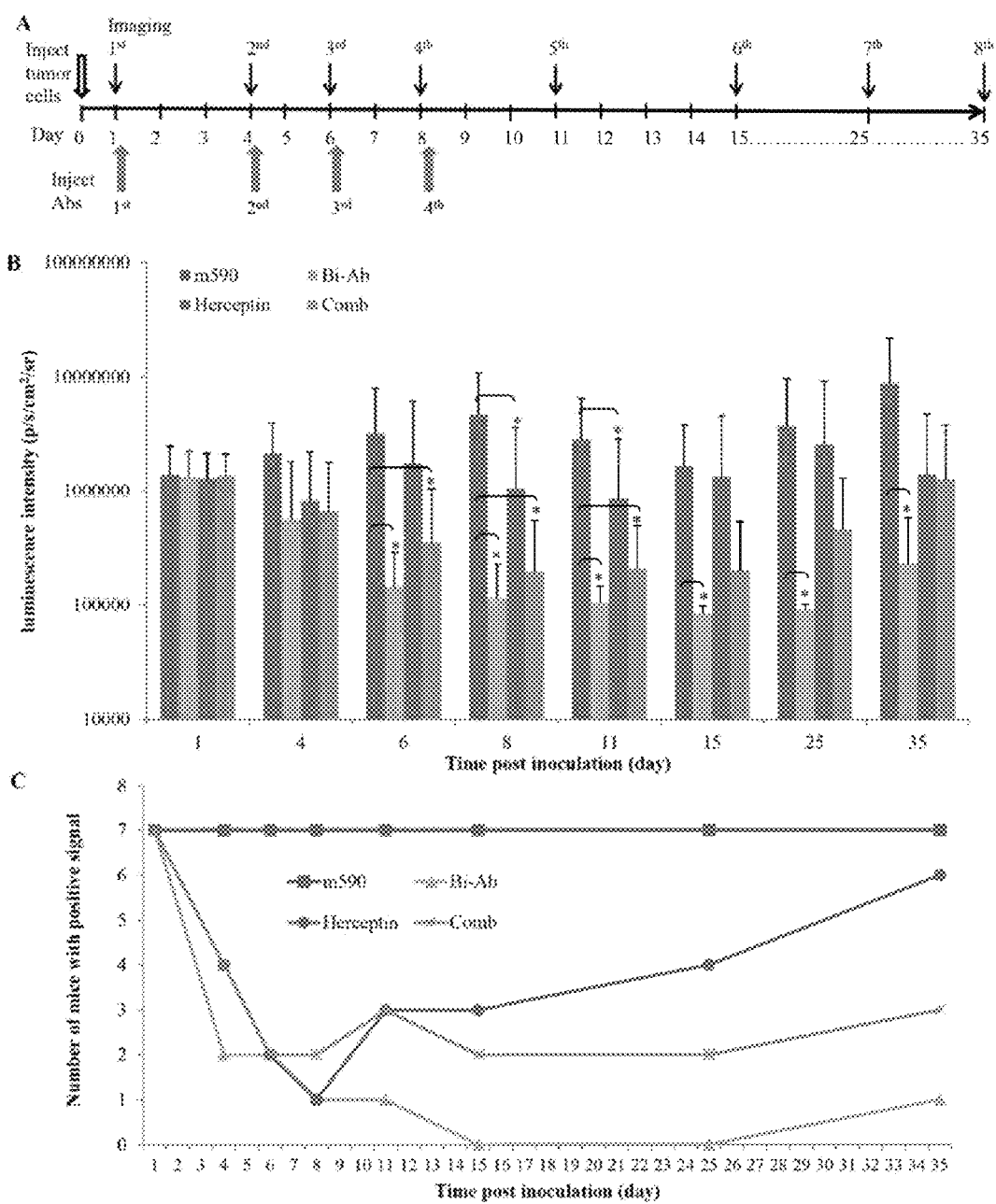
FIG. 4 shows inhibition of ovarian cancer growth by anti-HER2/anti-IGF-IR in SKOV-3 HER2- and IGF-IR-overexpressing xenograft mouse model in comparison with m590 and Herceptin alone or in combination. (A) Diagram of the mouse study. (B) Average luminescence intensities in each group of mice at different time points. Logarithmic values of the average luminescence intensities were used in ANOVA (one-way Analysis of Variance) statistical analysis to test if there was significant difference between any two groups at the same time point. Two paired groups with significant difference (P-value<0.001) are indicated. (C) Number of mice in each group with luminescence intensity 2-fold higher than the baseline level (no inoculation).

Enhancement of Growth-Inhibitory Activity of Anti-HER2/Anti-IGF-IR Antibodies 1N SKOV-3 Tumor Xenograft Mouse Model Mice bearing subcutaneous luciferase-expressing SKOV-3 tumors demonstrate efficient tumor regression after administration of anti-HER2/anti-IGF-IR antibodies. FIG. 4 shows luminescence intensity in SKOV-3 tumor-bearing mice at different time points after tumor inoculation and antibody treatment. Following i.p. injection of either Herceptin, m590, or anti-HER2/anti-IGF-IR antibodies on days 1, 4, 6, and 8 post tumor cell inoculation, the group that received anti-HER2/anti-IGF-IR antibodies showed the most prominent regression of tumor growth.

To establish a HER2- and IGF-IR-overexpressing cancer xenograft mouse model for testing the effect of Bi-Ab in vivo, we generated a SKOV-3-Luc cell line that stably expresses luciferase. We tested Bi-Ab, m590, Herceptin, and Comb in this mouse model following the protocol shown in FIG. 4A. There were four experimental groups in total, and each group had 7 nude mice. Three million of SKOV-3-Luc cells were injected subcutaneously to each nude mouse, and antibodies (100 µg per mouse) were injected by i.p. on days 1, 4, 6 and 8 post inoculations. Mouse body weight and luminescence intensity in the regions of interest (ROI) were measured on days 1, 4, 6 and 8 prior to antibody injections, and repeated on days 11, 15, 25 and 35 post inoculations. The average body weight of Bi-Ab treated mice did not decrease throughout the study, while the average mouse body weight of the other three experimental groups decreased on day 4. Nevertheless, there was no significant difference in average body weight among the 4 groups at comparable time points.

The average luminescence intensities varied across all the experimental groups (FIG. 4B). Notably, the Bi-Ab treated group experienced a dramatic inhibition of tumor growth which lasted for a much longer time compared to the other three groups. The average luminescence intensities in the Bi-Ab group were significantly lower than those of the m590 group on day 6 and thereafter (FIG. 4B).

The Comb group also showed lower average luminescence intensities than the m590 group on days 6, 8, and 11, but the Herceptin group only showed lower average luminescence intensities than the m590 group on days 8 and 11 (FIG. 4B). The average luminescence intensity of the m590 group also decreased on day 11, and further decreased on day 15, but returned to high levels on days 25 and 35. The Comb group showed relapse (increased average luminescence intensity) starting on day 25, while the Herceptin group relapsed earlier on day 15. The average luminescence intensity of the Bi-Ab on day 35 slightly increased, but it was still significantly lower than that of the m590 group (FIG. 4B).

We then investigated individual mice in each group and counted the number of mice that had 2-fold higher luminescence intensity than the baseline level (no inoculation) (FIG. 4C). The Bi-Ab group showed early decrease in luminescence intensity. 5 out 7 mice in the Bi-Ab group had luminescence intensities below 2-fold of the baseline level on day 4, while only 3 out 7 mice in the Comb and Herceptin groups had the same low levels of luminescence intensity on day 4 (FIG. 4C). The other two mice in the Bi-Ab showed luminescence intensities below 2-fold of the baseline level on days 8 and 15, and the luminescence intensities of all mice in Bi-Ab group remained low till the end of the study except that one mouse relapsed on day 35 (FIG. 4C). 5 out of 7 mice in the Comb group showed luminescence intensities below 2-fold of the baseline level on days 6 and 8, but one of these 5 mice in the Comb group relapsed on day 35.

6 out of 7 mice in the Herceptin group showed luminescence intensities below 2-fold of the baseline level on day 8, but these mice relapsed one by one as the study progressed. There was only one mouse left in the Herceptin group that had the luminescence intensity below 2-fold of the baseline level on day 35 (FIG. 4C). None of mice in the m590 ever exhibited luminescence intensity below 2-fold of the baseline level throughout the study. These results indicate that Bi-Ab more effectively inhibited cancer growth than m590 and Herceptin, as well as the combination of m590 and Herceptin. Furthermore, Bi-Ab efficiently postponed the relapse of HER2- and IGF-IR-overexpressing cancer.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

I claim:

1. An isolated, bi-specific antibody or a bi-specific binding fragment thereof that specifically binds to human epidermal growth factor receptor 2 (HER2) and human insulin-like growth factor I receptor (IGF-IR),
   wherein the isolated antibody or binding fragment thereof comprises the amino acid sequences SEQ ID NO: 1, SEQ ID NO: 2, SEQ ID NO: 3, and SEQ ID NO: 4, or antigen-binding fragments thereof, wherein at least two of the amino acid sequences comprise HER2 antigen binding regions and at least two of the amino acid sequences comprise IGF-IR antigen binding regions, and
   wherein the antibody or binding fragment thereof has little detectable reactivity or physical association with other proteins or structures.

2. The isolated antibody or binding fragment thereof according to claim 1, wherein CH3 of a constant region comprises SEQ ID NO: 5.

3. The isolated antibody or binding fragment thereof according to claim 1, wherein CH3 of a constant region comprises SEQ ID NO: 6.

4. The isolated antibody or binding fragment thereof according to claim 1, wherein CH3 of a constant region comprises SEQ ID NO: 7.

5. The isolated antibody or binding fragment thereof according to claim 1, which specifically binds to human HER2 and human IGF-IR expressed on tumor or cancer cells.

6. The isolated antibody or binding fragment thereof according to claim 1, which specifically binds to extracellular domains of human HER2 and human IGF-IR.

7. The isolated antibody or binding fragment thereof according to claim 1, which comprises an F(ab')$_2$.

8. The isolated antibody or binding fragment thereof according to claim 1, which is a humanized antibody.

9. A pharmaceutical composition comprising the isolated antibody or binding fragment thereof according to claim 1 and a pharmaceutically acceptable carrier.

10. A method for treating a tumor or cancer, comprising administering to a subject in need of such treatment an effective amount of the isolated antibody or binding fragment thereof according to claim 1.

11. The method according to claim 10, wherein the subject is a human.

12. The method according to claim 10, wherein the tumor or cancer is breast cancer, ovarian cancer, uterine cancer, prostate cancer, testicular germ cell tumor, glioblastoma multiforme, gastric cancer, esophagus cancer, lung cancer, liver cancer, and colon cancer.

13. A method of determining the presence of HER2 and/or IGF-IR in a mammal, comprising:
    obtaining a test sample from a mammal;
    contacting the test sample with the isolated antibody or binding fragment thereof according to claim 1; and
    determining whether the bi-specific antibody has bound, wherein binding of the bi-specific antibody indicates the presence of HER2 and/or IGF-IR in the mammal.

* * * * *